United States Patent
Zhu et al.

(10) Patent No.: US 11,788,082 B2
(45) Date of Patent: *Oct. 17, 2023

(54) T4 DNA LIGASE VARIANTS WITH INCREASED THERMOSTABILITY

(71) Applicant: AbClonal Science, Inc., Woburn, MA (US)

(72) Inventors: Zhenyu Zhu, Lynnfield, MA (US); Aine Quimby, Newburyport, MA (US); Dapeng Sun, Lexington, MA (US); Alicia DiCicco, Salem, MA (US)

(73) Assignee: ABclonal Science, Inc., Woburn, MA (US)

( * ) Notice: Subject to any disclaimer, the term of this patent is extended or adjusted under 35 U.S.C. 154(b) by 31 days.

This patent is subject to a terminal disclaimer.

(21) Appl. No.: 17/677,655

(22) Filed: Feb. 22, 2022

(65) Prior Publication Data
US 2023/0265412 A1  Aug. 24, 2023

(51) Int. Cl.
*C12N 9/00* (2006.01)
*C12P 19/34* (2006.01)

(52) U.S. Cl.
CPC ............... *C12N 9/93* (2013.01); *C12P 19/34* (2013.01); *C12Y 605/01001* (2013.01)

(58) Field of Classification Search
None
See application file for complete search history.

(56) References Cited

U.S. PATENT DOCUMENTS

| 10,640,812 | B2 * | 5/2020 | Crameri | C12Y 605/01001 |
| 10,837,009 | B1 | 11/2020 | Ong | |
| 11,685,913 | B1 * | 6/2023 | DiCicco | C12Q 1/6869 435/183 |

* cited by examiner

*Primary Examiner* — Richard G Hutson
(74) *Attorney, Agent, or Firm* — Eric P. Mirabel

(57) ABSTRACT

A number of T4 DNA ligase mutants exhibiting enhanced ligation activity at temperatures above 37° C. compared to the wild-type ligase were engineered, characterized, and selected via gel electrophoresis of ligation products from a standard ligation assay. T4 Ligase catalyzes the formation of phosphodiester bonds between the 5' and 3' ends of complementary cohesive ends or blunt ends of duplex DNA, a process that is vital to numerous molecular biology processes including cloning and sequencing.

5 Claims, 3 Drawing Sheets

Specification includes a Sequence Listing.

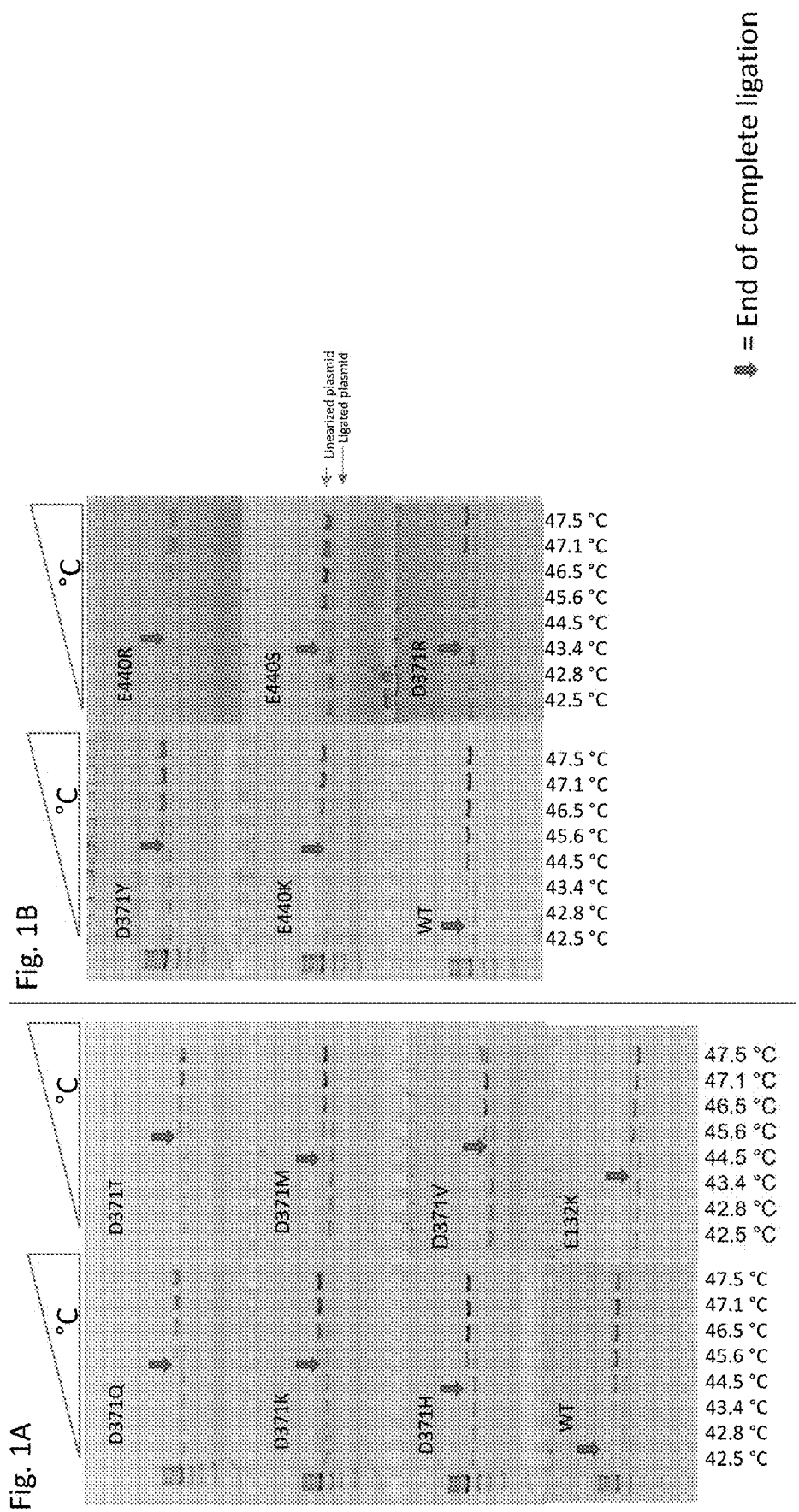
Figures 1A and 1B: T4 DNA Ligase Variants Displaying Increased Thermostability, Gradient 5 (composite image)

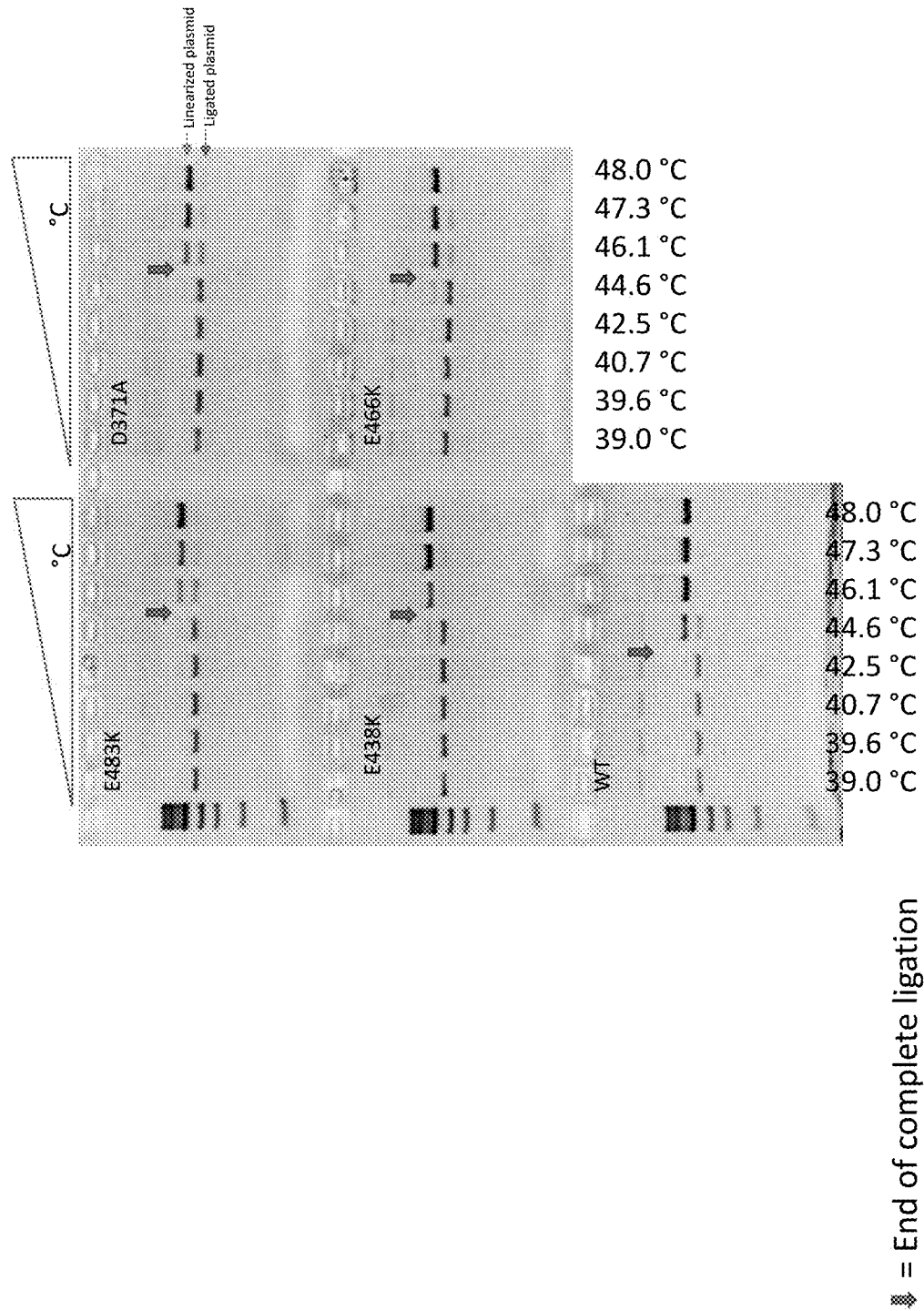
Figures 2: T4 DNA Ligase Variants Displaying Increased Thermostability, Gradient 4 (Composite image)
→ = End of complete ligation

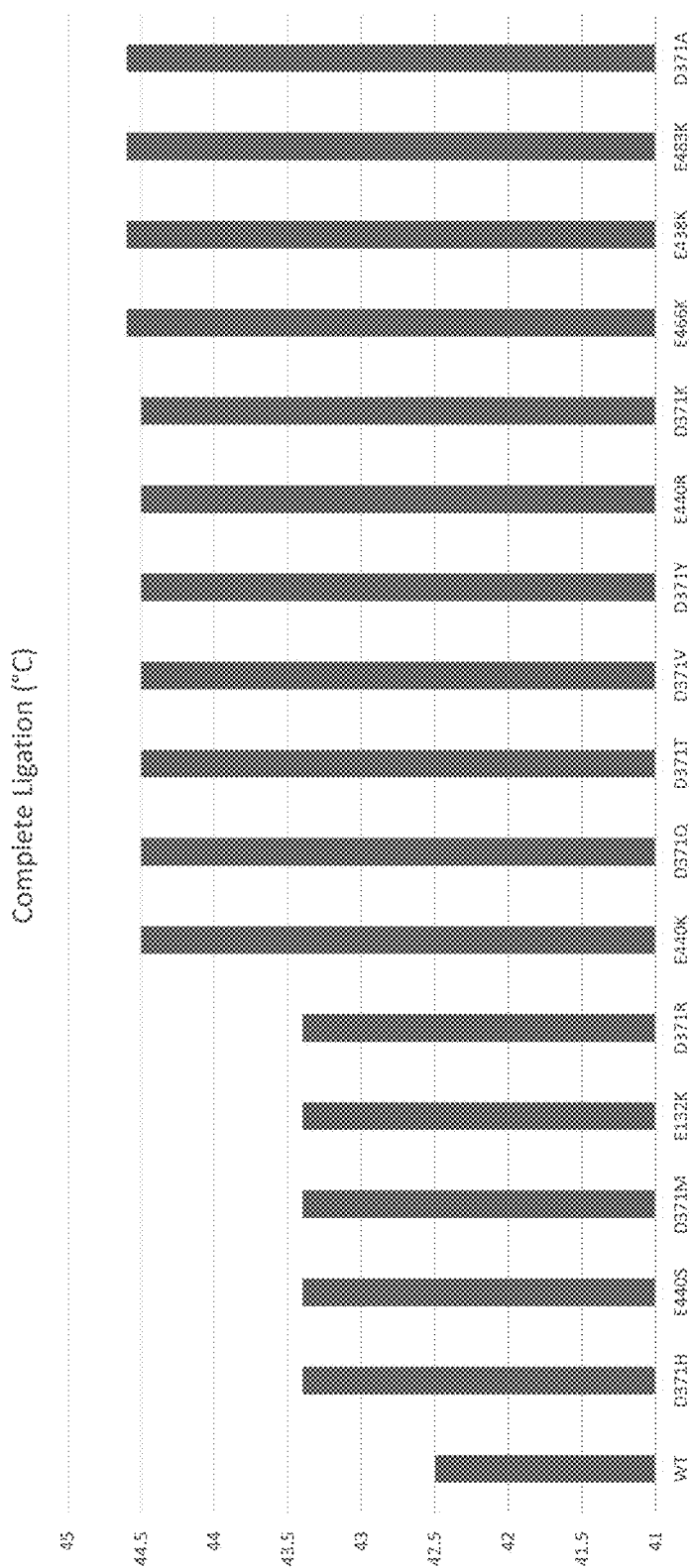

T4 DNA LIGASE VARIANTS WITH INCREASED THERMOSTABILITY

SEQUENCE LISTING

The instant application contains a Sequence Listing which has been submitted electronically in ASCII format and is hereby incorporated by reference in its entirety. Said ASCII copy, created on Mar. 9, 2022, is named ABCL-T4TEMP_SL.txt and is 111,074 bytes in size.

BACKGROUND

DNA ligases are integral repair proteins in living organisms that catalyze the repair of single-stranded breaks in duplex DNA. T4 DNA ligase utilizes the energy of the biomolecule ATP to repair nicked double-stranded DNA and also to join double-stranded DNA that has complementary single-strand overhangs (sticky or cohesive ends), as well as blunt-ended fragments, making it a useful tool for combining smaller DNA fragments to create double-stranded DNA constructs in vitro.

DNA ligases form phosphodiester bonds between duplex nucleic acid fragments at the intersection of juxtaposed 5' phosphate and 3' hydroxyl termini. By designing complementary overhangs between each of the double-stranded fragments, ligation can be directed to be both positionally specific and directionally oriented. This allows for specific integration of DNA or RNA fragments into larger vectors to meet the needs of molecular biology research. Out of the commercially available ligases, T4 DNA Ligase is a versatile enzyme that catalyzes the bond joining duplex DNA or RNA at both overhanging ends and blunt ends, has a rapid ligation speed, and via ligation, repairs the mismatches that exist in nicked DNA. Because it is the backbone of many molecular biology protocols and is in constant demand, it generates a large share of the revenue for many life science products companies due to its significance in the molecular biology reagent market.

Typically, wild type (WT) T4 DNA ligase is inhibited at temperatures greater than 37° C. with complete inhibition of ligation in most circumstances at or above 42° C. Studies of enzyme activity have indicated that while the inherent activity of T4 DNA ligase is optimal at 37° C., ligation yields are highest at 12-16° C.; as higher temperatures promote dissociation of the cohesive ends of substrate DNA and lower ligation efficiency. To balance between limiting dissociation and optimizing enzyme activity, most ligation procedures recommend temperatures between 16-25° C. for highest product yield. Typically, ligation is part of a multi-step protocol in molecular biology research, and ligation with T4 DNA ligase must be performed separately from other enzymatic reaction steps that require higher temperatures. Separating reactions in research protocols adds time and complexity to experiments and increases opportunity for sample loss or contamination. Thus, combined ("one-pot") reactions are preferable. In addition to increasing ease of use, thermostable T4 DNA ligase variants have robust potential for developing novel molecular biology applications due to greater temperature tolerance.

SUMMARY

T4 DNA ligase mutants exhibiting enhanced ligation activity at increased reaction temperatures compared to the wild-type ligase were engineered, characterized, and selected via gel electrophoresis of ligation products from a standard ligation assay. Wild-type (WT) ligase catalyzes the formation of phosphodiester bonds between the 5' and 3' ends of complementary cohesive ends or blunt ends of duplex DNA. Typically, WT T4 DNA ligase performs best when ligations take place at temperatures between 16° C. and 37° C., with most protocols suggesting between 16-25° C. depending upon variables of time and substrate type. Increasing the reaction temperature above 42.5° C. significantly inhibits efficiency of WT T4 DNA ligase, with even partial ligation ceasing at around 42° C., depending on other reaction conditions such as ligase concentration, substrate type, substrate concentration, and buffer. Thermostable variants of WT T4 DNA ligase show greater activity at higher temperatures, retaining ability for complete ligation above the temperatures that inhibit wild-type activity. These thermostable variants can be used in wider applications than WT T4 FNA ligase, which is limited by its sensitivity to higher temperatures.

The 17 variants with increased ligation efficiency at elevated temperatures include E132K (SEQ ID NO:4), D371A (SEQ ID NO:6), D371H (SEQ ID NO:8), D371K (SEQ ID NO:10), D371M (SEQ ID NO:12), D371Q (SEQ ID NO:14), D371R (SEQ ID NO:16), D371T (SEQ ID NO:18), D371V (SEQ ID NO:20), D371Y (SEQ ID NO:22), E438K (SEQ ID NO:24), E440K (SEQ ID NO:26), E440R (SEQ ID NO:28), E440S (SEQ ID NO:30), E466K (SEQ ID NO:32) and E483K (SEQ ID NO:34). The DNA sequence for each mutant and for WT is shown in the sequence listing and assigned the immediately preceding odd numbered sequence identification number to the even-numbered sequence identification number for the amino acid sequence of each mutant above (which each have a six-membered His tag (SEQ ID NO: 35) and an eight-membered Gly, Leu, Gly, Ser tag at the C-terminus). The maximum ligation efficiencies for all listed mutants were presented in Gradients 4 and 5, which are shown in the figures below.

BRIEF DESCRIPTION OF THE DRAWINGS

FIGS. 1A and 1B show a composite gel (agarose, 1.2%) image of the identified variants compared to wild-type in Temperature Gradient 5, which ranges between 42.5 and 47.5° C. Separate reactions containing 200 ng ligase and 10 ng substrate were incubated at 8 different temperatures (see Table 2) for 60 minutes for each mutant or wild-type. Downward-pointing arrows indicate the point after which complete ligation is considered inhibited.

FIG. 1A shows WT and the images for the variants D371H, D371K, D371M, D371Q, E132K, D371V, and D371T.

FIG. 1B shows WT and the images for the variants E440K and D371Y.

FIG. 2 shows a composite gel (agarose, 1.2%) image of the identified variants E438K, E466K, E483K, and D371A compared to wild-type in Temperature Gradient 4, which ranges between 39° C. and 48° C. Separate reactions containing 200 ng ligase and 10 ng substrate were incubated at 8 different temperatures (see Table 2) for 60 minutes for each mutant or wild-type. Downward-pointing arrows indicate the point after which complete ligation is considered inhibited.

FIG. 3 shows a graphical representation the data found in Table 1, which used compiled data for each temperature across the gradient sets to identify maximum temperature thresholds for each variant. Each enzyme has a bar indicating the point after which complete ligation is considered inhibited, as determined though DNA gel visualization of ligation product.

TABLE 1

Maximum Ligation Thresholds

| | Complete Ligation (° C.) |
|---|---|
| WT | 42.5 |
| D371H | 43.4 |
| E440S | 43.4 |
| D371M | 43.4 |
| E132K | 43.4 |
| D371R | 43.4 |
| E440K | 44.5 |
| D371Q | 44.5 |
| D371T | 44.5 |
| D371V | 44.5 |
| D371Y | 44.5 |
| E440R | 44.5 |
| D371K | 44.5 |
| E466K | 44.6 |
| E438K | 44.6 |
| E483K | 44.6 |
| D371A | 44.6 |

TABLE 2

Temperature Gradients: Specific Temperatures Tested (° C.)

| Gradient | 1 | 2 | 3 | 4 | 5 | 6 | 7 | 8 |
|---|---|---|---|---|---|---|---|---|
| 4 | 48 | 47.3 | 46.1 | 44.6 | 42.5 | 40.7 | 39.6 | 39 |
| 5 | 47.5 | 47.1 | 46.5 | 45.6 | 44.5 | 43.4 | 42.8 | 42.5 |

DETAILED DESCRIPTION

The term "biologically active fragment" refers to any fragment, derivative, homolog or analog of a T4 DNA ligase mutant that possesses in vivo or in vitro activity that is characteristic of that biomolecule; including, for example, ligase activity or repairing via ligation the mismatches that exist in nicked DNA. In some embodiments, the biologically active fragment, derivative, homolog or analog of the mutant T4 DNA ligase possesses any degree of the biological activity of the mutant T4 DNA ligase in any in vivo or in vitro assay of interest.

In some embodiments, the biologically active fragment can optionally include any number of contiguous amino acid residues of the mutant T4 DNA ligase. The invention also includes the polynucleotides encoding any such biologically active fragment.

Biologically active fragments can arise from post transcriptional processing or from translation of alternatively spliced RNAs, or alternatively can be created through engineering, bulk synthesis, or other suitable manipulation. Biologically active fragments include fragments expressed in native or endogenous cells as well as those made in expression systems such as, for example, in bacterial, yeast, plant, insect or mammalian cells.

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) supra). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

When referring to a gene, "mutant" means the gene has at least one base (nucleotide) change, deletion, or insertion with respect to a native or wild type gene. The mutation (change, deletion, and/or insertion of one or more nucleotides) can be in the coding region of the gene or can be in an intron, 3' UTR, 5' UTR, or promoter region. As nonlimiting examples, a mutant gene can be a gene that has an insertion within the promoter region that can either increase or decrease expression of the gene; can be a gene that has a deletion, resulting in production of a nonfunctional protein, truncated protein, dominant negative protein, or no protein; or, can be a gene that has one or more point mutations leading to a change in the amino acid of the encoded protein or results in aberrant splicing of the gene transcript.

The terms "mutant T4 DNA ligase of the invention" and "mutant T4 DNA ligase" when used in this Detailed Description section refer to, depending on the context, collectively or individually, the mutant T4 DNA Ligase polypeptides tested and exhibiting significant ligation activity in the presence of temperatures sufficient to significantly decrease the ligation activity of the wild type T4 DNA Ligase, which are: E132K (SEQ ID NO:4), D371A (SEQ ID NO:6), D371H (SEQ ID NO:8), D371K (SEQ ID NO:10), D371M (SEQ ID NO:12), D371Q (SEQ ID NO:14), D371R (SEQ ID NO:16), D371T (SEQ ID NO:18), D371V (SEQ ID NO:20), D371Y (SEQ ID NO:22), E438K (SEQ ID NO:24), E440K (SEQ ID NO:26), E440R (SEQ ID NO:28), E440S (SEQ ID NO:30), E466K (SEQ ID NO:32) and E483K (SEQ ID NO:34) (but without the six-membered His tag (SEQ ID NO: 35) and the eight-membered Gly, Leu, Gly, Ser tag at the C-terminus), and/or Variant Sequences and/or Degenerate Nucleic Acid Sequences, as those terms are defined in the Summary section.

"Naturally-occurring" or "wild-type" refers to the form found in nature. For example, a naturally occurring or wild-type polypeptide or polynucleotide sequence is a sequence present in an organism, which has not been intentionally modified by human manipulation.

The terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), Proc. Natl. Acad. Sci. USA 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), Nature Genetics 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), Proc. Natl. Acad. Sci. USA 89, 10915-10919), recommended for query sequences over 85 units in length (nucleotide bases or amino acids).

In some embodiments, the invention relates to methods (and related kits, systems, apparatuses and compositions) for performing a ligation reaction comprising or consisting of contacting a mutant T4 DNA ligase or a biologically active fragment thereof with a nucleic acid template in the presence of one or more nucleotides, and ligating at least one of the one or more nucleotides using the mutant T4 DNA ligase or the biologically active fragment thereof.

In some embodiments, the method can include ligating a double stranded RNA or DNA polynucleotide strand into a circular molecule. In some embodiments, the method can further include detecting a signal indicating the ligation by using a sensor. In some embodiments, the sensor is an ISFET. In some embodiments, the sensor can include a detectable label or detectable reagent within the ligating reaction.

In some embodiments, the invention relates to methods (and related kits, systems, apparatus and compositions) for performing rolling circle amplification (see U.S. Pat. No. 5,714,320, incorporated by reference) of a nucleic acid, using the mutant T4 DNA ligase as the enzyme in the ligation steps of the amplification process. The amplifying includes amplifying the nucleic acid in solution, as well as clonally amplifying the nucleic acid on a solid support such as a nucleic acid bead, flow cell, nucleic acid array, or wells present on the surface of the solid support.

Making Mutant T4 DNA Ligase

The mutant T4 DNA ligase of the invention can be expressed in any suitable host system, including a bacterial, yeast, fungal, baculovirus, plant or mammalian host cell. For bacterial host cells, suitable promoters for directing transcription of the nucleic acid constructs of the present disclosure, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proc. Natl Acad. Sci. USA 75: 3727-3731), as well as the tac promoter (DeBoer et al., 1983, Proc. Natl Acad. Sci. USA 80: 21-25).

For filamentous fungal host cells, suitable promoters for directing the transcription of the nucleic acid constructs of the present disclosure include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8:423-488.

For baculovirus expression, insect cell lines derived from Lepidopterans (moths and butterflies), such as *Spodoptera frugiperda*, are used as host. Gene expression is under the control of a strong promoter, e.g., pPolh.

Plant expression vectors are based on the Ti plasmid of *Agrobacterium tumefaciens*, or on the tobacco mosaic virus (TMV), potato virus X, or the cowpea mosaic virus. A commonly used constitutive promoter in plant expression vectors is the cauliflower mosaic virus (CaMV) 35S promoter.

For mammalian expression, cultured mammalian cell lines such as the Chinese hamster ovary (CHO), COS, including human cell lines such as HEK and HeLa may be used to produce the mutant T4 DNA ligase. Examples of mammalian expression vectors include the adenoviral vectors, the pSV and the pCMV series of plasmid vectors, vaccinia and retroviral vectors, as well as baculovirus. The promoters for cytomegalovirus (CMV) and SV40 are commonly used in mammalian expression vectors to drive gene expression. Non-viral promoters, such as the elongation factor (EF)-1 promoter, are also known.

The control sequence for the expression may also be a suitable transcription terminator sequence, that is, a sequence recognized by a host cell to terminate transcription. The terminator sequence is operably linked to the 3' terminus of the nucleic acid sequence encoding the polypeptide. Any terminator which is functional in the host cell of choice may be used.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase.

Terminators for insect, plant and mammalian host cells are also well known.

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, Microbiol Rev 57: 109-137.

Effective signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells can be from the genes for *Saccharomyces cerevisiae* alpha-factor and *Saccharomyces cerevisiae* invertase. Signal peptides for other host cell systems are also well known.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the mutant T4 DNA ligase relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter. Regulatory systems for other host cells are also well known.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the KRED polypeptide of the present invention would be operably linked with the regulatory sequence.

Another embodiment includes a recombinant expression vector comprising a polynucleotide encoding an engineered mutant T4 DNA ligase or a variant thereof, and one or more expression regulating regions such as a promoter and a terminator, and a replication origin, depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the mutant T4 DNA ligase at such sites.

Alternatively, the nucleic acid sequences of the mutant T4 DNA ligase may be expressed by inserting the nucleic acid sequences or a nucleic acid construct comprising the sequences into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the mutant T4 DNA ligase polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector herein preferably contain one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Suitable markers for yeast host cells are ADE2, HIS3, LEU2, LYS2, METS, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*. Selectable markers for insect, plant and mammalian cells are also well known.

The expression vectors of the present invention preferably contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location(s) in the chromosome(s). The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A ori, or the origins of replication of plasmids pBR322, pUC19, pACYC177 (which plasmid has the P15A ori), or pACYC184 permitting replication in *E. coli*, and pUB110, pE194, pTA1060, or pAM31 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it's functioning temperature-sensitive in the host cell (see, e.g., Ehrlich, 1978, Proc Natl Acad Sci. USA 75:1433).

More than one copy of a nucleic acid sequence of the mutant T4 DNA ligase may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Expression vectors for the mutant T4 DNA ligase polynucleotide are commercially available. Suitable commercial expression vectors include p3×FLAG™ expression vectors from Sigma-Aldrich Chemicals, St. Louis Mo., which includes a CMV promoter and hGH polyadenylation site for expression in mammalian host cells and a pBR322 origin of replication and ampicillin resistance markers for amplification in *E. coli*. Other suitable expression vectors are pBluescriptII SK(−) and pBK-CMV, which are commercially available from Stratagene, LaJolla Calif., and plasmids which are derived from pBR322 (Gibco BRL), pUC (Gibco BRL), pREP4, pCEP4 (Invitrogen) or pPoly (Lathe et al., 1987, Gene 57:193-201).

Suitable host cells for expression of a polynucleotide encoding the mutant T4 DNA ligase, are well known in the art and include but are not limited to, bacterial cells, such as *E. coli, Lactobacillus kefir, Lactobacillus brevis, Lactobacillus minor, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture mediums and growth conditions for the above-described host cells are well known in the art.

Polynucleotides for expression of the mutant T4 DNA ligase may be introduced into cells by various methods known in the art. Techniques include among others, electroporation, biolistic particle bombardment, liposome mediated transfection, calcium chloride transfection, and protoplast fusion. Various methods for introducing polynucleotides into cells are known to the skilled artisan.

Polynucleotides encoding the mutant T4 DNA ligase can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides can be prepared by chemical synthesis using, e.g., the classical phosphoramidite method described by Beaucage et al., 1981, Tet Lett 22:1859-69, or the method described by Matthes et al., 1984, EMBO J. 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources, such as The Midland Certified Reagent Company, Midland, Tex., The Great American Gene Company, Ramona, Calif., ExpressGen Inc. Chicago, Ill., and Operon Technologies Inc., Alameda, Calif.

Engineered the mutant T4 DNA ligase expressed in a host cell can be recovered from the cells and or the culture medium using any one or more of the well-known techniques for protein purification, including, among others, lysozyme treatment, sonication, filtration, salting-out, ultra-centrifugation, and chromatography. Suitable solutions for lysing and the high efficiency extraction of proteins from bacteria, such as E. coli, are commercially available under the trade name CelLytic B™ from Sigma-Aldrich of St. Louis Mo.

Chromatographic techniques for isolation of the mutant T4 DNA ligase include, among others, reverse phase chromatography high performance liquid chromatography, ion exchange chromatography, gel electrophoresis, and affinity chromatography. Conditions for purification will depend, in part, on factors such as net charge, hydrophobicity, hydrophilicity, molecular weight, molecular shape, and will be apparent to those having skill in the art.

In some embodiments, affinity techniques may be used to isolate the mutant T4 DNA ligase. For affinity chromatography purification, any antibody which specifically binds the mutant T4 DNA ligase may be used. For the production of antibodies, various host animals, including but not limited to rabbits, mice, rats, etc., may be immunized by injection with a compound. The compound may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette Guerin) and *Corynebacterium parvum*.

Example of Making Heat-Stable T4 DNA Ligase Mutants:

Heat-stable T4 DNA ligase mutants were generated by conventional inverse PCR mutagenesis. All mutants are sequenced verified, expressed in *E. Coli*, and purified. All T4 DNA ligase mutants and the WT T4 DNA ligase have an added C-terminal His tag for ease of purification.

Ligation Substrate was Prepared by the Following Procedure:

The DNA vector used was pUC19 (New England Bio Labs, catalog number N3041S). PUC19 is a double stranded circle that is 2686 base pairs long. PUC19 was digested with BsaI-HF®v2 (New England Bio Labs, catalog number R3733S) which has a recognition sequence of 5'-GGTCTC (N1)/(N5)-3' and makes one cut in the pUC19. 5 µl of puC19 at a concentration of 1 mg/ml was combined with 2.5 µl of 20,000 units/ml BsaI-HF®v2, 5 µl 10× rCutSmart™ Buffer (New England Bio Labs, catalog number B6004S) (50 mM Potassium Acetate, 20 mM Tris-acetate, 10 mM Magnesium Acetate, 100 µg/ml Recombinant Albumin), and 35 µl of water. After all components were combined the combined solution was incubated at 37° C. to allow digestion to take place. After one hour at 37° C., the reaction was incubated at 80° C. for 20 minutes to heat inactivate the BsaI-HF®v2 and stop digestion. The mixture was then diluted with water to a concentration of 10 ng/µl.

The Ligation Screening Procedure was Performed as Follows:

Stock concentration of each ligase sample, wild-type or variant, was 100 ng/µl. Initial screening tested all variants en masse, comparing mutant to wild-type activity in reactions at 37° C., 42° C., 45° C., and 47.5° C. For each reaction, 2 ul (200 ng) of enzyme was pipetted, in duplicate, into individual wells of a PCR plate. To each well, a master mix consisting of 1× T4 DNA Ligase Reaction Buffer (New England Biolabs, catalog number B0202A: 50 mM Tris-HCl, 10 mM $MgCl_2$, 1 mM ATP, 10 mM DTT), 10 ng substrate (pUC19 digested with BsaI-HF®v2), plus sufficient water to make the total volume per reaction 20 µl, was added. The reactions were incubated at the indicated temperature (37° C., 42° C., 45° C., or 47.5° C.) for 60 minutes on a BioRad T100 Thermal Cycler. After the 60-minute incubation period, the reactions received a heat shock at 80° C. for 2 minutes to stop any further activity. Additionally, 4 µl of stop solution (120 mM EDTA, 30% glycerol, 50 mM Tris-HCl pH 8.0, 0.0125% bromophenol blue, 0.1% SDS, and 5×Gel Red Nucleic Acid Stain (Biotium, Fremont, CA)) was added to every reaction.

Gel electrophoresis was performed using 1.2% agarose gels run at 180V for 40 minutes. Each gel displayed a wild-type T4 DNA ligase sample and 47 variant T4 DNA ligase samples, in duplicate. Variants that suggested greater thermostability by completing ligation more effectively than WT each temperature were identified for secondary screening and confirmation.

Secondary screening involved challenging each previously selected mutant, as well as wild-type, with a temperature gradient programmed into the thermal cycler, which calculates 6 additional temperatures between a low and high temperature specified by the user, and assigns each member of 8 rows with 12 samples per row, a temperature along the gradient. Several gradients were tested, allowing for identification of thermostability differences down to 0.1° C. For every reaction plate, 8 identical wild-type samples and 8 identical variant samples for 11 separate variants were loaded such that each enzyme had a sample exposed to all 8 of the temperatures along the heat-block of the thermal cycler, for direct comparison. The specific temperatures used in each gradient set tested are listed in Table 1. Each reaction contained 200 ng total protein (2 µl stock protein), plus 16 µl of a master mix consisting of 1× T4 DNA Ligase Reaction Buffer (New England Biolabs, catalog number B0202A: 50 mM Tris-HCl, 10 mM $MgCl_2$, 1 mM ATP, 10 mM DTT), 10 ng substrate, and sufficient water to achieve total volume per reaction of 20 µl. The ligation reactions were incubated on the temperature gradient (see Table 2 for details) for 60 minutes, then subjected to a heat shock at 80° C. for 2 minutes to stop any further activity. Finally, 6 µl of stop solution (120 mM EDTA, 30% glycerol, 50 mM Tris-HCl pH 8.0, 0.0125% bromophenol blue, 0.1% SDS, and 5× Gel Red Nucleic Acid Stain (Biotium, Fremont, CA)) was added to every reaction.

Gel electrophoresis was performed using 1.2% agarose gels run at 180V for 40 minutes. Each gel displayed a wild-type T4 DNA ligase sample and 11 variant T4 DNA ligase samples, each showing activity from low to high temperature over gel 8 lanes. Data comparing partial and complete activity for each variant and wild-type over all the temperatures used in each of the gradients was compiled and compared, and variants exhibiting increased ligation efficiency, for complete ligation, compared to wild-type T4 DNA ligase at each temperature were identified. Table 2 lists the T4 DNA Ligase variants that performed better than WT, generating complete ligation products at temperatures higher than wild-type enzyme could sustain. The maximum temperature at which complete ligation is observed for each enzyme is provided.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, including but not limited to Variant Sequences, and that such modifications and variations are considered to be within the scope of this invention as defined by the appended claims.

```
T4 DNA Ligase CH Wild Type DNA
                                                                  SEQ ID NO: 1
      1   ATGATTCTTAAAATTCTGAACGAAATAGCATCTATTGGTTCAACTAAACAGAAGCAAGCA      60

61   ATTCTTGAAAAGAATAAAGATAATGAATTGCTTAAACGAGTATATCGTCTGACTTATTCT     120

121   CGTGGGTTACAGTATTATATCAAGAAATGGCCTAAACCTGGTATTGCTACCCAGAGTTTT     180

181   GGAATGTTGACTCTTACCGATATGCTTGACTTCATTGAATTCACATTAGCTACTCGGAAA     240

241   TTGACTGGAAATGCAGCAATTGAGGAATTAACTGGATATATCACCGATGGTAAAAAAGAT     300

301   GATGTTGAAGTTTTGCGTCGAGTGATGATGCGAGACCTTGAATGTGGTGCTTCAGTATCT     360

361   ATTGCAAACAAAGTTTGGCCAGGTTTAATTCCTGAACAACCTCAAATGCTCGCAAGTTCT     420

421   TATGATGAAAAGGCATTAATAAGAATATCAAATTTCCAGCCTTTGCTCAGTTAAAAGCT     480

481   GATGGAGCTCGGTGTTTTGCTGAAGTTAGAGGTGATGAATTAGATGATGTTCGTCTTTTA     540

541   TCACGAGCTGGTAATGAATATCTAGGATTAGATCTTCTTAAGGAAGAGTTAATTAAAATG     600

601   ACCGCTGAAGCCCGCCAGATTCATCCAGAAGGTGTGTTGATTGATGGCGAATTGGTATAC     660

661   CATGAGCAAGTTAAAAAGGAGCCAGAAGGCCTAGATTTTCTTTTTGATGCTTATCCTGAA     720

721   AACAGTAAAGCTAAAGAATTCGCCGAAGTAGCTGAATCACGTACTGCTTCTAATGGAATC     780

781   GCCAATAAATCTTTAAAGGGAACCATTTCTGAAAAAGAAGCACAATGCATGAAGTTTCAG     840

841   GTCTGGGATTATGTCCCGTTGGTAGAAATATACAGTCTTCCTGCATTTCGTTTGAAATAT     900

901   GATGTACGTTTTTCTAAACTAGAACAAATGACATCTGGATATGATAAAGTAATTTTAATT     960

961   GAAAACCAGGTAGTAAATAACCTAGATGAAGCTAAGGTAATTTATAAAAAGTATATTGAC    1020

1021   CAAGGTCTTGAAGGTATTATTCTCAAAAATATCGATGGATTATGGGAAAATGCTCGTTCA    1080

1081   AAAAATCTTTATAAATTTAAAGAAGTAATTGATGTTGATTTAAAAATTGTAGGAATTTAT    1140
```

-continued

```
         1141  CCTCACCGTAAAGACCCTACTAAAGCGGGTGGATTTATTCTTGAGTCAGAGTGTGGAAAA    1200

1201  ATTAAGGTAAATGCTGGTTCAGGCTTAAAAGATAAAGCCGGTGTAAAATCGCATGAACTT    1260

1261  GACCGTACTCGCATTATGGAAAACCAAAATTATTATATTGGAAAAATTCTAGAGTGCGAA    1320

1321  TGCAACGGTTGGTTAAAATCTGATGGCCGCACTGATTACGTTAAATTATTTCTTCCGATT    1380

1381  GCGATTCGTTTACGTGAAGATAAAACTAAAGCTAATACATTCGAAGATGTATTTGGTGAT    1440

1441  TTTCATGAGGTAACTGGTCTAGGTTCTGGCAGTTCAGGTCATCACCACCATCATCACTAA    1500
```

T4 DNA Ligase CH Wild Type Protein

SEQ ID NO: 2

```
            1  MILKILNEIASIGSTKQKQAILEKNKDNELLKRVYRLTYSRGLQYYIKKWPKPGIATQSF      60

61  GMLTLTDMLDFIEFTLATRKLIGNAAIEELTGYITDGKKDDVEVLRRVMMRDLECGASVS     120

121  IANKVWPGLIPEQPQMLASSYDEKGINKNIKFPAFAQLKADGARCFAEVRGDELDDVRLL     180

181  SRAGNEYLGLDLLKEELIKMTAEARQIHPEGVLIDGELVYHEQVKKEPEGLDFLFDAYPE     240

241  NSKAKEFAEVAESRTASNGIANKSLKGTISEKEAQCMKFQVWDYVPLVEIYSLPAFRLKY     300

301  DVRFSKLEQMTSGYDKVILIENQVVNNLDEAKVIYKKYIDQGLEGIILKNIDGLWENARS     360

361  KNLYKFKEVIDVDLKIVGIYPHRKDPTKAGGFILESECGKIKVNAGSGLKDKAGVKSHEL     420

421  DRTRIMENQNYYIGKILECECNGWLKSDGRTDYVKLFLPIAIRLREDKTKANTFEDVFGD     480

481  FHEVTGLGSGSSGHHHHHH*                                           499
```

T4 DNA Ligase CH E132K DNA

SEQ ID NO: 3

```
            1  ATGATTCTTAAAATTCTGAACGAAATAGCATCTATTGGTTCAACTAAACAGAAGCAAGCA      60

61  ATTCTTGAAAAGAATAAAGATAATGAATTGCTTAAACGAGTATATCGTCTGACTTATTCT     120

121  CGTGGGTTACAGTATTATATCAAGAAATGGCCTAAACCTGGTATTGCTACCCAGAGTTTT     180

181  GGAATGTTGACTCTTACCGATATGCTTGACTTCATTGAATTCACATTAGCTACTCGGAAA     240

241  TTGACTGGAAATGCAGCAATTGAGGAATTAACTGGATATATCACCGATGGTAAAAAGAT      300

301  GATGTTGAAGTTTTGCGTCGAGTGATGATGCGAGACCTTGAATGTGGTGCTTCAGTATCT     360

361  ATTGCAAACAAAGTTTGGCCAGGTTTAATTCCTAAACAACCTCAAATGCTCGCAAGTTCT     420

421  TATGATGAAAAGGCATTAATAAGAATATCAAATTTCCAGCCTTTGCTCAGTTAAAAGCT      480

481  GATGGAGCTCGGTGTTTTGCTGAAGTTAGAGGTGATGAATTAGATGATGTTCGTCTTTTA     540

541  TCACGAGCTGGTAATGAATATCTAGGATTAGATCTTCTTAAGGAAGAGTTAATTAAAATG     600

601  ACCGCTGAAGCCCGCCAGATTCATCCAGAAGGTGTGTTGATTGATGGCGAATTGGTATAC     660

661  CATGAGCAAGTTAAAAAGGAGCCAGAAGGCCTAGATTTTCTTTTTGATGCTTATCCTGAA     720

721  AACAGTAAAGCTAAAGAATTCGCCGAAGTAGCTGAATCACGTACTGCTTCTAATGGAATC     780

781  GCCAATAAATCTTTAAAGGGAACCATTTCTGAAAAAGAAGCACAATGCATGAAGTTTCAG     840

841  GTCTGGGATTATGTCCCGTTGGTAGAAATATACAGTCTTCCTGCATTTCGTTTGAAATAT     900

901  GATGTACGTTTTTCTAAACTAGAACAAATGACATCTGGATATGATAAAGTAATTTTAATT     960

961  GAAAACCAGGTAGTAAATAACCTAGATGAAGCTAAGGTAATTTATAAAAAGTATATTGAC    1020

1021  CAAGGTCTTGAAGGTATTATTCTCAAAAATATCGATGGATTATGGGAAAATGCTCGTTCA    1080

1081  AAAAATCTTTATAAATTTAAAGAAGTAATTGATGTTGATTTAAAAATTGTAGGAATTTAT    1140

1141  CCTCACCGTAAAGACCCTACTAAAGCGGGTGGATTTATTCTTGAGTCAGAGTGTGGAAAA    1200

1201  ATTAAGGTAAATGCTGGTTCAGGCTTAAAAGATAAAGCCGGTGTAAAATCGCATGAACTT    1260

1261  GACCGTACTCGCATTATGGAAAACCAAAATTATTATATTGGAAAAATTCTAGAGTGCGAA    1320

1321  TGCAACGGTTGGTTAAAATCTGATGGCCGCACTGATTACGTTAAATTATTTCTTCCGATT    1380
```

```
1381  GCGATTCGTTTACGTGAAGATAAAACTAAAGCTAATACATTCGAAGATGTATTTGGTGAT   1440

1441  TTTCATGAGGTAACTGGTCTAGGTTCTGGCAGTTCAGGTCATCACCACCATCATCACTAA   1500
```

T4 DNA Ligase CH E132K Protein

SEQ ID NO: 4

```
  1  MILKILNEIASIGSTKQKQAILEKNKDNELLKRVYRLTYSRGLQYYIKKWPKPGIATQSF    60

61  GMLTLTDMLDFIEFTLATRKLTGNAAIEELTGYITDGKKDDVEVLRRVMMRDLECGASVS   120

121  IANKVWPGLIPKQPQMLASSYDEKGINKNIKFPAFAQLKADGARCFAEVRGDELDDVRLL   180

181  SRAGNEYLGLDLLKEELIKMTAEARQIHPEGVLIDGELVYHEQVKKEPEGLDFLFDAYPE   240

241  NSKAKEFAEVAESRTASNGIANKSLKGTISEKEAQCMKFQVWDYVPLVEIYSLPAFRLKY   300

301  DVRFSKLEQMTSGYDKVILIENQVVNNLDEAKVIYKKYIDQGLEGIILKNIDGLWENARS   360

361  KNLYKFKEVIDVDLKIVGIYPHRKDPTKAGGFILESECGKIKVNAGSGLKDKAGVKSHEL   420

421  DRTRIMENQNYYIGKILECECNGWLKSDGRTDYVKLFLPIAIRLREDKTKANTFEDVFGD   480

481  FHEVTGLGSGSSGHHHHHH*                                          499
```

T4 DNA Ligase CH D371A DNA

SEQ ID NO: 5

```
  1  ATGATTCTTAAAATTCTGAACGAAATAGCATCTATTGGTTCAACTAAACAGAAGCAAGCA    60

61  ATTCTTGAAAAGAATAAAGATAATGAATTGCTTAAACGAGTATATCGTCTGACTTATTCT   120

121  CGTGGGTTACAGTATTATATCAAGAAATGGCCTAAACCTGGTATTGCTACCCAGAGTTTT   180

181  GGAATGTTGACTCTTACCGATATGCTTGACTTCATTGAATTCACATTAGCTACTCGGAAA   240

241  TTGACTGGAAATGCAGCAATTGAGGAATTAACTGGATATATCACCGATGGTAAAAAAGAT   300

301  GATGTTGAAGTTTTGCGTCGAGTGATGATGCGAGACCTTGAATGTGGTGCTTCAGTATCT   360

361  ATTGCAAACAAAGTTTGGCCAGGTTTAATTCCTGAACAACCTCAAATGCTCGCAAGTTCT   420

421  TATGATGAAAAGGCATTAATAAGAATATCAAATTTCCAGCCTTTGCTCAGTTAAAAGCT   480

481  GATGGAGCTCGGTGTTTTGCTGAAGTTAGAGGTGATGAATTAGATGATGTTCGTCTTTTA   540

541  TCACGAGCTGGTAATGAATATCTAGGATTAGATCTTCTTAAGGAAGAGTTAATTAAAATG   600

601  ACCGCTGAAGCCCGCCAGATTCATCCAGAAGGTGTGTTGATTGATGGCGAATTGGTATAC   660

661  CATGAGCAAGTTAAAAAGGAGCCAGAAGGCCTAGATTTTCTTTTTGATGCTTATCCTGAA   720

721  AACAGTAAAGCTAAAGAATTCGCCGAAGTAGCTGAATCACGTACTGCTTCTAATGGAATC   780

781  GCCAATAAATCTTTAAAGGGAACCATTTCTGAAAAAGAAGCACAATGCATGAAGTTTCAG   840

841  GTCTGGGATTATGTCCCGTTGGTAGAAATATACAGTCTTCCTGCATTTCGTTTGAAATAT   900

901  GATGTACGTTTTTCTAAACTAGAACAAATGACATCTGGATATGATAAAGTAATTTTAATT   960

961  GAAAACCAGGTAGTAAATAACCTAGATGAAGCTAAGGTAATTTATAAAAAGTATATTGAC  1020

1021 CAAGGTCTTGAAGGTATTATTCTCAAAAATATCGATGGATTATGGGAAAATGCTCGTTCA  1080

1081 AAAAATCTTTATAAATTTAAAGAAGTAATTGCAGTTGATTTAAAAATTGTAGGAATTTAT  1140

1141 CCTCACCGTAAAGACCCTACTAAAGCGGGTGGATTTATTCTTGAGTCAGAGTGTGGAAAA  1200

1201 ATTAAGGTAAATGCTGGTTCAGGCTTAAAAGATAAAGCCGGTGTAAAATCGCATGAACTT  1260

1261 GACCGTACTCGCATTATGGAAAACCAAAATTATTATATTGGAAAAATTCTAGAGTGCGAA  1320

1321 TGCAACGGTTGGTAAAATCTGATGGCCGCACTGATTACGTTAAATTATTTCTTCCGATT  1380

1381 GCGATTCGTTTACGTGAAGATAAAACTAAAGCTAATACATTCGAAGATGTATTTGGTGAT  1440

1441 TTTCATGAGGTAACTGGTCTAGGTTCTGGCAGTTCAGGTCATCACCACCATCATCACTAA  1500
```

T4 DNA Ligase CH D371A Protein

SEQ ID NO: 6

```
  1  MILKILNEIASIGSTKQKQAILEKNKDNELLKRVYRLTYSRGLQYYIKKWPKPGIATQSF       60
 61  GMLTLTDMLDFIEFTLATRKLTGNAAIEELTGYITDGKKDDVEVLRRVMMRDLECGASVS      120
121  IANKVWPGLIPEQPQMLASSYDEKGINKNIKFPAFAQLKADGARCFAEVRGDELDDVRLL      180
181  SRAGNEYLGLDLLKEELIKMTAEARQIHPEGVLIDGELVYHEQVKKEPEGLDFLFDAYPE      240
241  NSKAKEFAEVAESRTASNGIANKSLKGTISEKEAQCMKFQVWDYVPLVEIYSLPAFRLKY      300
301  DVRFSKLEQMTSGYDKVILIENQVVNNLDEAKVIYKKYIDQGLEGIILKNIDGLWENARS      360
361  KNLYKFKEVIAVDLKIVGIYPHRKDPTKAGGFILESECGKIKVNAGSGLKDKAGVKSHEL      420
421  DRTRIMENQNYYIGKILECECNGWLKSDGRTDYVKLFLPIAIRLREDKTKANTFEDVFGD      480
481  FHEVTGLGSGSSGHHHHHH*                                             499
```

T4 DNA Ligase CH D371H DNA

SEQ ID NO: 7

```
   1  ATGATTCTTAAAATTCTGAACGAAATAGCATCTATTGGTTCAACTAAACAGAAGCAAGCA      60
  61  ATTCTTGAAAAGAATAAAGATAATGAATTGCTTAAACGAGTATATCGTCTGACTTATTCT     120
 121  CGTGGGTTACAGTATTATATCAAGAAATGGCCTAAACCTGGTATTGCTACCCAGAGTTTT     180
 181  GGAATGTTGACTCTTACCGATATGCTTGACTTCATTGAATTCACATTAGCTACTCGGAAA     240
 241  TTGACTGGAAATGCAGCAATTGAGGAATTAACTGGATATATCACCGATGGTAAAAAAGAT     300
 301  GATGTTGAAGTTTTGCGTCGAGTGATGATGCGAGACCTTGAATGTGGTGCTTCAGTATCT     360
 361  ATTGCAAACAAAGTTTGGCCAGGTTTAATTCCTGAACAACCTCAAATGCTCGCAAGTTCT     420
 421  TATGATGAAAAGGCATTAATAAGAATATCAAATTTCCAGCCTTTGCTCAGTTAAAAGCT     480
 481  GATGGAGCTCGGTGTTTTGCTGAAGTTAGAGGTGATGAATTAGATGATGTTCGTCTTTTA     540
 541  TCACGAGCTGGTAATGAATATCTAGGATTAGATCTTCTTAAGGAAGAGTTAATTAAAATG     600
 601  ACCGCTGAAGCCCGCCAGATTCATCCAGAAGGTGTGTTGATTGATGGCGAATTGGTATAC     660
 661  CATGAGCAAGTTAAAAAGGAGCCAGAAGGCCTAGATTTTCTTTTTGATGCTTATCCTGAA     720
 721  AACAGTAAAGCTAAAGAATTCGCCGAAGTAGCTGAATCACGTACTGCTTCTAATGGAATC     780
 781  GCCAATAAATCTTTAAAGGGAACCATTTCTGAAAAAGAAGCACAATGCATGAAGTTTCAG     840
 841  GTCTGGGATTATGTCCCGTTGGTAGAAATATACAGTCTTCCTGCATTTCGTTTGAAATAT     900
 901  GATGTACGTTTTTCTAAACTAGAACAAATGACATCTGGATATGATAAAGTAATTTTAATT     960
 961  GAAAACCAGGTAGTAAATAACCTAGATGAAGCTAAGGTAATTTATAAAAAGTATATTGAC    1020
1021  CAAGGTCTTGAAGGTATTATTCTCAAAAATATCGATGGATTATGGGAAAATGCTCGTTCA    1080
1081  AAAAATCTTTATAAATTTAAAGAAGTAATTCATGTTGATTTAAAAATTGTAGGAATTTAT    1140
1141  CCTCACCGTAAAGACCCTACTAAAGCGGGTGGATTTATTCTTGAGTCAGAGTGTGGAAAA    1200
1201  ATTAAGGTAAATGCTGGTTCAGGCTTAAAAGATAAGCCGGTGTAAAATCGCATGAACTT    1260
1261  GACCGTACTCGCATTATGGAAAACCAAATTATTATATTGGAAAAATTCTAGAGTGCGAA    1320
1321  TGCAACGGTTGGTTAAAATCTGATGGCCGCACTGATTACGTTAAATTATTTCTTCCGATT    1380
1381  GCGATTCGTTTACGTGAAGATAAAACTAAAGCTAATACATTCGAAGATGTATTTGGTGAT    1440
1441  TTTCATGAGGTAACTGGTCTAGGTTCTGGCAGTTCAGGTCATCACCACCATCATCACTAA    1500
```

T4 DNA Ligase CH D371H Protein

SEQ ID NO: 8

```
  1  MILKILNEIASIGSTKQKQAILEKNKDNELLKRVYRLTYSRGLQYYIKKWPKPGIATQSF       60
 61  GMLTLTDMLDFIEFTLATRKLTGNAAIEELTGYITDGKKDDVEVLRRVMMRDLECGASVS      120
121  IANKVWPGLIPEQPQMLASSYDEKGINKNIKFPAFAQLKADGARCFAEVRGDELDDVRLL      180
```

-continued

```
    181 SRAGNEYLGLDLLKEELIKMTAEARQIHPEGVLIDGELVYHEQVKKEPEGLDFLFDAYPE    240
    241 NSKAKEFAEVAESRTASNGIANKSLKGTISEKEAQCMKFQVWDYVPLVEIYSLPAFRLKY    300
    301 DVRFSKLEQMTSGYDKVILIENQVVNNLDEAKVIYKKYIDQGLEGIILKNIDGLWENARS    360
    361 KNLYKFKEVIHVDLKIVGIYPHRKDPTKAGGFILESECGKIKVNAGSGLKDKAGVKSHEL    420
    421 DRTRIMENQNYYIGKILECECNGWLKSDGRTDYVKLFLPIAIRLREDKTKANTFEDVFGD    480
    481 FHEVTGLGSGSSGHHHHHH*                                            499
```

T4 DNA Ligase CH D371K DNA

SEQ ID NO: 9
```
      1 ATGATTCTTAAAATTCTGAACGAAATAGCATCTATTGGTTCAACTAAACAGAAGCAAGCA     60
     61 ATTCTTGAAAAGAATAAAGATAATGAATTGCTTAAACGAGTATATCGTCTGACTTATTCT    120
    121 CGTGGGTTACAGTATTATATCAAGAAATGGCCTAAACCTGGTATTGCTACCCAGAGTTTT    180
    181 GGAATGTTGACTCTTACCGATATGCTTGACTTCATTGAATTCACATTAGCTACTCGGAAA    240
    241 TTGACTGGAAATGCAGCAATTGAGGAATTAACTGGATATATCACCGATGGTAAAAAAGAT    300
    301 GATGTTGAAGTTTTGCGTCGAGTGATGATGCGAGACCTTGAATGTGGTGCTTCAGTATCT    360
    361 ATTGCAAACAAAGTTTGGCCAGGTTTAATTCCTGAACAACCTCAAATGCTCGCAAGTTCT    420
    421 TATGATGAAAAGGCATTAATAAGAATATCAAATTTCCAGCCTTTGCTCAGTTAAAAGCT    480
    481 GATGGAGCTCGGTGTTTTGCTGAAGTTAGAGGTGATGAATTAGATGATGTTCGTCTTTTA    540
    541 TCACGAGCTGGTAATGAATATCTAGGATTAGATCTTCTTAAGGAAGAGTTAATTAAAATG    600
    601 ACCGCTGAAGCCCGCCAGATTCATCCAGAAGGTGTGTTGATTGATGGCGAATTGGTATAC    660
    661 CATGAGCAAGTTAAAAAGGAGCCAGAAGGCCTAGATTTTCTTTTTGATGCTTATCCTGAA    720
    721 AACAGTAAAGCTAAAGAATTCGCCGAAGTAGCTGAATCACGTACTGCTTCTAATGGAATC    780
    781 GCCAATAAATCTTTAAAGGGAACCATTTCTGAAAAGAAGCACAATGCATGAAGTTTCAG    840
    841 GTCTGGGATTATGTCCCGTTGGTAGAAATATACAGTCTTCCTGCATTTCGTTTGAAATAT    900
    901 GATGTACGTTTTTCTAAACTAGAACAAATGACATCTGGATATGATAAAGTAATTTTAATT    960
    961 GAAAACCAGGTAGTAAATAACCTAGATGAAGCTAAGGTAATTTATAAAAAGTATATTGAC   1020
   1021 CAAGGTCTTGAAGGTATTATTCTCAAAAATATCGATGGATTATGGGAAAATGCTCGTTCA   1080
   1081 AAAAATCTTTATAAATTTAAAGAAGTAATTAAAGTTGATTTAAAAATTGTAGGAATTTAT   1140
   1141 CCTCACCGTAAAGACCCTACTAAAGCGGGTGGATTTATTCTTGAGTCAGAGTGTGGAAAA   1200
   1201 ATTAAGGTAAATGCTGGTTCAGGCTTAAAAGATAAAGCCGGTGTAAAATCGCATGAACTT   1260
   1261 GACCGTACTCGCATTATGGAAAACCAAAATTATTATATTGGAAAAATTCTAGAGTGCGAA   1320
   1321 TGCAACGGTTGGTTAAAATCTGATGGCCGCACTGATTACGTTAAATTATTTCTTCCGATT   1380
   1381 GCGATTCGTTTACGTGAAGATAAAACTAAAGCTAATACATTCGAAGATGTATTTGGTGAT   1440
   1441 TTTCATGAGGTAACTGGTCTAGGTTCTGGCAGTTCAGGTCATCACCACCATCATCACTAA   1500
```

T4 DNA Ligase CH D371K Protein

SEQ ID NO: 10
```
      1 MILKILNEIASIGSTKQKQAILEKNKDNELLKRVYRLTYSRGLQYYIKKWPKPGIATQSF     60
     61 GMLTLTDMLDFIEFTLATRKLTGNAAIEELTGYITDGKKDDVEVLRRVMMRDLECGASVS    120
    121 IANKVWPGLIPEQPQMLASSYDEKGINKNIKFPAFAQLKADGARCFAEVRGDELDDVRLL    180
    181 SRAGNEYLGLDLLKEELIKMTAEARQIHPEGVLIDGELVYHEQVKKEPEGLDFLFDAYPE    240
    241 NSKAKEFAEVAESRTASNGIANKSLKGTISEKEAQCMKFQVWDYVPLVEIYSLPAFRLKY    300
    301 DVRFSKLEQMTSGYDKVILIENQVVNNLDEAKVIYKKYIDQGLEGIILKNIDGLWENARS    360
```

-continued

```
    361  KNLYKFKEVIKVDLKIVGIYPHRKDPTKAGGFILESECGKIKVNAGSGLKDKAGVKSHEL    420
    421  DRTRIMENQNYYIGKILECECNGWLKSDGRTDYVKLFLPIAIRLREDKTKANTFEDVFGD    480
    481  FHEVTGLGSGSSGHHHHHH*                                          499
```

T4 DNA Ligase CH D371M DNA

SEQ ID NO: 11

```
      1  ATGATTCTTAAAATTCTGAACGAAATAGCATCTATTGGTTCAACTAAACAGAAGCAAGCA    60
     61  ATTCTTGAAAAGAATAAAGATAATGAATTGCTTAAACGAGTATATCGTCTGACTTATTCT    120
    121  CGTGGGTTACAGTATTATATCAAGAAATGGCCTAAACCTGGTATTGCTACCCAGAGTTTT    180
    181  GGAATGTTGACTCTTACCGATATGCTTGACTTCATTGAATTCACATTAGCTACTCGGAAA    240
    241  TTGACTGGAAATGCAGCAATTGAGGAATTAACTGGATATATCACCGATGGTAAAAAGAT     360
    301  GATGTTGAAGTTTTGCGTCGAGTGATGATGCGAGACCTTGAATGTGGTGCTTCAGTATCT    420
    361  ATTGCAAACAAAGTTTGGCCAGGTTTAATTCCTGAACAACCTCAAATGCTCGCAAGTTCT    300
    421  TATGATGAAAAGGCATTAATAAGAATATCAAATTTCCAGCCTTTGCTCAGTTAAAAGCT     480
    481  GATGGAGCTCGGTGTTTTGCTGAAGTTAGAGGTGATGAATTAGATGATGTTCGTCTTTTA    540
    541  TCACGAGCTGGTAATGAATATCTAGGATTAGATCTTCTTAAGGAAGAGTTAATTAAAATG    600
    601  ACCGCTGAAGCCCGCCAGATTCATCCAGAAGGTGTGTTGATTGATGGCGAATTGGTATAC    660
    661  CATGAGCAAGTTAAAAAGGAGCCAGAAGGCCTAGATTTTCTTTTTGATGCTTATCCTGAA    720
    721  AACAGTAAAGCTAAAGAATTCGCCGAAGTAGCTGAATCACGTACTGCTTCTAATGGAATC    780
    781  GCCAATAAATCTTTAAAGGGAACCATTTCTGAAAAAGAAGCACAATGCATGAAGTTTCAG    840
    841  GTCTGGGATTATGTCCCGTTGGTAGAAATATACAGTCTTCCTGCATTTCGTTTGAAATAT    900
    901  GATGTACGTTTTTCTAAACTAGAACAAATGACATCTGGATATGATAAAGTAATTTTAATT    960
    961  GAAAACCAGGTAGTAAATAACCTAGATGAAGCTAAGGTAATTTATAAAAAGTATATTGAC    1020
   1021  CAAGGTCTTGAAGGTATTATTCTCAAAAATATCGATGGATTATGGGAAAATGCTCGTTCA    1080
   1081  AAAAATCTTTATAAATTTAAAGAAGTAATTATGGTTGATTTAAAAATTGTAGGAATTTAT    1140
   1141  CCTCACCGTAAAGACCCTACTAAAGCGGGTGGATTTATTCTTGAGTCAGAGTGTGGAAAA    1200
   1201  ATTAAGGTAAATGCTGGTTCAGGCTTAAAAGATAAAGCCGGTGTAAAATCGCATGAACTT    1260
   1261  GACCGTACTCGCATTATGGAAAACCAAAATTATTATATTGGAAAAATTCTAGAGTGCGAA    1320
   1321  TGCAACGGTTGGTAAAATCTGATGGCCGCACTGATTACGTTAAATTATTTCTTCCGATT     1380
   1381  GCGATTCGTTTACGTGAAGATAAAACTAAAGCTAATACATTCGAAGATGTATTTGGTGAT    1440
   1441  TTTCATGAGGTAACTGGTCTAGGTTCTGGCAGTTCAGGTCATCACCACCATCATCACTAA    1500
```

T4 DNA Ligase CH D371M Protein

SEQ ID NO: 12

```
      1  MILKILNEIASIGSTKQKQAILEKNKDNELLKRVYRLTYSRGLQYYIKKWPKPGIATQSF    60
     61  GMLTLTDMLDFIEFTLATRKLTGNAAIEELTGYITDGKKDDVEVLRRVMMRDLECGASVS    120
    121  IANKVWPGLIPEQPQMLASSYDEKGINKNIKFPAFAQLKADGARCFAEVRGDELDDVRLL    180
    181  SRAGNEYLGLDLLKEELIKMTAEARQIHPEGVLIDGELVYHEQVKKEPEGLDFLFDAYPE    240
    241  NSKAKEFAEVAESRTASNGIANKSLKGTISEKEAQCMKFQVWDYVPLVEIYSLPAFRLKY    300
    301  DVRFSKLEQMTSGYDKVILIENQVVNNLDEAKVIYKKYIDQGLEGIILKNIDGLWENARS    360
    361  KNLYKFKEVIMVDLKIVGIYPHRKDPTKAGGFILESECGKIKVNAGSGLKDKAGVKSHEL    420
    421  DRTRIMENQNYYIGKILECECNGWLKSDGRTDYVKLFLPIAIRLREDKTKANTFEDVFG     480
    481  FHEVTGLGSGSSGHHHHHH*                                          499
```

-continued

T4 DNA Ligase CH D371Q DNA
SEQ ID NO: 13

```
   1  ATGATTCTTAAAATTCTGAACGAAATAGCATCTATTGGTTCAACTAAACAGAAGCAAGCA     60
  61  ATTCTTGAAAAGAATAAAGATAATGAATTGCTTAAACGAGTATATCGTCTGACTTATTCT    120
 121  CGTGGGTTACAGTATTATATCAAGAAATGGCCTAAACCTGGTATTGCTACCCAGAGTTTT    180
 181  GGAATGTTGACTCTTACCGATATGCTTGACTTCATTGAATTCACATTAGCTACTCGGAAA    240
 241  TTGACTGGAAATGCAGCAATTGAGGAATTAACTGGATATATCACCGATGGTAAAAAAGAT    300
 301  GATGTTGAAGTTTTGCGTCGAGTGATGATGCGAGACCTTGAATGTGGTGCTTCAGTATCT    360
 361  ATTGCAAACAAAGTTTGGCCAGGTTTAATTCCTGAACAACCTCAAATGCTCGCAAGTTCT    420
 421  TATGATGAAAAGGCATTAATAAGAATATCAAATTTCCAGCCTTTGCTCAGTTAAAAGCT    480
 481  GATGGAGCTCGGTGTTTTGCTGAAGTTAGAGGTGATGAATTAGATGATGTTCGTCTTTTA    540
 541  TCACGAGCTGGTAATGAATATCTAGGATTAGATCTTCTTAAGGAAGAGTTAATTAAAATG    600
 601  ACCGCTGAAGCCCGCCAGATTCATCCAGAAGGTGTGTTGATTGATGGCGAATTGGTATAC    660
 661  CATGAGCAAGTTAAAAAGGAGCCAGAAGGCCTAGATTTTCTTTTTGATGCTTATCCTGAA    720
 721  AACAGTAAAGCTAAAGAATTCGCCGAAGTAGCTGAATCACGTACTGCTTCTAATGGAATC    780
 781  GCCAATAAATCTTTAAAGGGAACCATTTCTGAAAAAGAAGCACAATGCATGAAGTTTCAG    840
 841  GTCTGGGATTATGTCCCGTTGGTAGAAATATACAGTCTTCCTGCATTTCGTTTGAAATAT    900
 901  GATGTACGTTTTTCTAAACTAGAACAAATGACATCTGGATATGATAAAGTAATTTTAATT    960
 961  GAAAACCAGGTAGTAAATAACCTAGATGAAGCTAAGGTAATTTATAAAAAGTATATTGAC   1020
1021  CAAGGTCTTGAAGGTATTATTCTCAAAAATATCGATGGATTATGGGAAAATGCTCGTTCA   1080
1081  AAAAATCTTTATAAATTTAAAGAAGTAATTCAAGTTGATTTAAAAATTGTAGGAATTTAT   1140
1141  CCTCACCGTAAAGACCCTACTAAAGCGGGTGGATTTATTCTTGAGTCAGAGTGTGGAAAA   1200
1201  ATTAAGGTAAATGCTGGTTCAGGCTTAAAAGATAAAGCCGGTGTAAAATCGCATGAACTT   1260
1261  GACCGTACTCGCATTATGGAAAACCAAAATTATTATATTGGAAAAATTCTAGAGTGCGAA   1320
1321  TGCAACGGTTGGTTAAAATCTGATGGCCGCACTGATTACGTTAAATTATTTCTTCCGATT   1380
1381  GCGATTCGTTTACGTGAAGATAAAACTAAAGCTAATACATTCGAAGATGTATTTGGTGAT   1440
1441  TTTCATGAGGTAACTGGTCTAGGTTCTGGCAGTTCAGGTCATCACCACCATCATCACTAA   1500
```

T4 DNA Ligase CH D371Q Protein
SEQ ID NO: 14

```
  1  MILKILNEIASIGSTKQKQAILEKNKDNELLKRVYRLTYSRGLQYYIKKWPKPGIATQSF     60
 61  GMLTLTDMLDFIEFTLATRKLTGNAAIEELTGYITDGKKDDVEVLRRVMMRDLECGASVS    120
121  IANKVWPGLIPEQPQMLASSYDEKGINKNIKFPAFAQLKADGARCFAEVRGDELDDVRLL    180
181  SRAGNEYLGLDLLKEELIKMTAEARQIHPEGVLIDGELVYHEQVKKEPEGLDFLFDAYPE    240
241  NSKAKEFAEVAESRTASNGIANKSLKGTISEKEAQCMKFQVWDYVPLVEIYSLPAFRLKY    300
301  DVRFSKLEQMTSGYDKVILIENQVVNNLDEAKVIYKKYIDQGLEGIILKNIDGLWENARS    360
361  KNLYKFKEVIQVDLKIVGIYPHRKDPTKAGGFILESECGKIKVNAGSGLKDKAGVKSHEL    420
421  DRTRIMENQNYYIGKILECECNGWLKSDGRTDYVKLFLPIAIRLREDKTKANTFEDVFGD    480
481  FHEVTGLGSGSSGHHHHHH*                                           499
```

T4 DNA Ligase CH D371R DNA
SEQ ID NO: 15

```
   1  ATGATTCTTAAAATTCTGAACGAAATAGCATCTATTGGTTCAACTAAACAGAAGCAAGCA     60
  61  ATTCTTGAAAAGAATAAAGATAATGAATTGCTTAAACGAGTATATCGTCTGACTTATTCT    120
 121  CGTGGGTTACAGTATTATATCAAGAAATGGCCTAAACCTGGTATTGCTACCCAGAGTTTT    180
```

-continued

```
 181  GGAATGTTGACTCTTACCGATATGCTTGACTTCATTGAATTCACATTAGCTACTCGGAAA        240
 241  TTGACTGGAAATGCAGCAATTGAGGAATTAACTGGATATATCACCGATGGTAAAAAGAT        300
 301  GATGTTGAAGTTTTGCGTCGAGTGATGATGCGAGACCTTGAATGTGGTGCTTCAGTATCT        360
 361  ATTGCAAACAAAGTTTGGCCAGGTTTAATTCCTGAACAACCTCAAATGCTCGCAAGTTCT        420
 421  TATGATGAAAAGGCATTAATAAGAATATCAAATTTCCAGCCTTTGCTCAGTTAAAAGCT        480
 481  GATGGAGCTCGGTGTTTTGCTGAAGTTAGAGGTGATGAATTAGATGATGTTCGTCTTTTA        540
 541  TCACGAGCTGGTAATGAATATCTAGGATTAGATCTTCTTAAGGAAGAGTTAATTAAAATG        600
 601  ACCGCTGAAGCCCGCCAGATTCATCCAGAAGGTGTGTTGATTGATGGCGAATTGGTATAC        660
 661  CATGAGCAAGTTAAAAAGGAGCCAGAAGGCCTAGATTTTCTTTTTGATGCTTATCCTGAA        720
 721  AACAGTAAAGCTAAAGAATTCGCCGAAGTAGCTGAATCACGTACTGCTTCTAATGGAATC        780
 781  GCCAATAAATCTTTAAAGGGAACCATTTCTGAAAAAGAAGCACAATGCATGAAGTTTCAG        840
 841  GTCTGGGATTATGTCCCGTTGGTAGAAATATACAGTCTTCCTGCATTTCGTTTGAAATAT        900
 901  GATGTACGTTTTTCTAAACTAGAACAAATGACATCTGGATATGATAAAGTAATTTTAATT        960
 961  GAAAACCAGGTAGTAAATAACCTAGATGAAGCTAAGGTAATTTATAAAAAGTATATTGAC       1020
1021  CAAGGTCTTGAAGGTATTATTCTCAAAAATATCGATGGATTATGGGAAAATGCTCGTTCA       1080
1081  AAAAATCTTTATAAATTTAAAGAAGTAATTCGTGTTGATTTAAAAATTGTAGGAATTTAT       1140
1141  CCTCACCGTAAAGACCCTACTAAAGCGGGTGGATTTATTCTTGAGTCAGAGTGTGGAAAA       1200
1201  ATTAAGGTAAATGCTGGTTCAGGCTTAAAAGATAAAGCCGGTGTAAAATCGCATGAACTT       1260
1261  GACCGTACTCGCATTATGGAAAACCAAAATTATTATATTGGAAAAATTCTAGAGTGCGAA       1320
1321  TGCAACGGTTGGTTAAAATCTGATGGCCGCACTGATTACGTTAAATTATTTCTTCCGATT       1380
1381  GCGATTCGTTTACGTGAAGATAAAACTAAAGCTAATACATTCGAAGATGTATTTGGTGAT       1440
1441  TTTCATGAGGTAACTGGTCTAGGTTCTGGCAGTTCAGGTCATCACCACCATCATCACTAA       1500
```

T4 DNA Ligase CH D371R Protein
SEQ ID NO: 16
```
  1  MILKILNEIASIGSTKQKQAILEKNKDNELLKRVYRLTYSRGLQYYIKKWPKPGIATQSF         60
 61  GMLTLTDMLDFIEFTLATRKLTGNAAIEELTGYITDGKKDDVEVLRRVMMRDLECGASVS        120
121  IANKVWPGLIPEQPQMLASSYDEKGINKNIKFPAFAQLKADGARCFAEVRGDELDDVRLL        180
181  SRAGNEYLGLDLLKEELIKMTAEARQIHPEGVLIDGELVYHEQVKKEPEGLDFLFDAYPE        240
241  NSKAKEFAEVAESRTASNGIANKSLKGTISEKEAQCMKFQVWDYVPLVEIYSLPAFRLKY        300
301  DVRFSKLEQMTSGYDKVILIENQVVNNLDEAKVIYKKYIDQGLEGIILKNIDGLWENARS        360
361  KNLYKFKEVIRVDLKIVGIYPHRKDPTKAGGFILESECGKIKVNAGSGLKDKAGVKSHEL        420
421  DRTRIMENQNYYIGKILECECNGWLKSDGRTDYVKLFLPIAIRLREDKTKANTFEDVFGD        480
481  FHEVTGLGSGSSGHHHHHH*                                                499
```

T4 DNA Ligase CH D371T DNA
SEQ ID NO: 17
```
  1  ATGATTCTTAAAATTCTGAACGAAATAGCATCTATTGGTTCAACTAAACAGAAGCAAGCA         60
 61  ATTCTTGAAAAGAATAAAGATAATGAATTGCTTAAACGAGTATATCGTCTGACTTATTCT        120
121  CGTGGGTTACAGTATTATATCAAGAAATGGCCTAAACCTGGTATTGCTACCCAGAGTTTT        180
181  GGAATGTTGACTCTTACCGATATGCTTGACTTCATTGAATTCACATTAGCTACTCGGAAA        240
241  TTGACTGGAAATGCAGCAATTGAGGAATTAACTGGATATATCACCGATGGTAAAAAGAT         300
301  GATGTTGAAGTTTTGCGTCGAGTGATGATGCGAGACCTTGAATGTGGTGCTTCAGTATCT        360
361  ATTGCAAACAAAGTTTGGCCAGGTTTAATTCCTGAACAACCTCAAATGCTCGCAAGTTCT        420
421  TATGATGAAAAGGCATTAATAAGAATATCAAATTTCCAGCCTTTGCTCAGTTAAAAGCT         480
```

-continued

```
 481  GATGGAGCTCGGTGTTTTGCTGAAGTTAGAGGTGATGAATTAGATGATGTTCGTCTTTTA    540
 541  TCACGAGCTGGTAATGAATATCTAGGATTAGATCTTCTTAAGGAAGAGTTAATTAAAATG    600
 601  ACCGCTGAAGCCCGCCAGATTCATCCAGAAGGTGTGTTGATTGATGGCGAATTGGTATAC    660
 661  CATGAGCAAGTTAAAAAGGAGCCAGAAGGCCTAGATTTTCTTTTTGATGCTTATCCTGAA    720
 721  AACAGTAAAGCTAAAGAATTCGCCGAAGTAGCTGAATCACGTACTGCTTCTAATGGAATC    780
 781  GCCAATAAATCTTTAAAGGGAACCATTTCTGAAAAAGAAGCACAATGCATGAAGTTTCAG    840
 841  GTCTGGGATTATGTCCCGTTGGTAGAAATATACAGTCTTCCTGCATTTCGTTTGAAATAT    900
 901  GATGTACGTTTTTCTAAACTAGAACAAATGACATCTGGATATGATAAAGTAATTTTAATT    960
 961  GAAAACCAGGTAGTAAATAACCTAGATGAAGCTAAGGTAATTTATAAAAGTATATTGAC   1020
1021  CAAGGTCTTGAAGGTATTATTCTCAAAAATATCGATGGATTATGGGAAAATGCTCGTTCA   1080
1081  AAAAATCTTTATAAATTTAAAGAAGTAATTACTGTTGATTTAAAAATTGTAGGAATTTAT   1140
1141  CCTCACCGTAAAGACCCTACTAAAGCGGGTGGATTTATTCTTGAGTCAGAGTGTGGAAAA   1200
1201  ATTAAGGTAAATGCTGGTTCAGGCTTAAAAGATAAAGCCGGTGTAAAATCGCATGAACTT   1260
1261  GACCGTACTCGCATTATGGAAAACCAAAATTATTATATTGGAAAAATTCTAGAGTGCGAA   1320
1321  TGCAACGGTTGGTTAAAATCTGATGGCCGCACTGATTACGTTAAATTATTTCTTCCGATT   1380
1381  GCGATTCGTTTACGTGAAGATAAAACTAAAGCTAATACATTCGAAGATGTATTTGGTGAT   1440
1441  TTTCATGAGGTAACTGGTCTAGGTTCTGGCAGTTCAGGTCATCACCACCATCATCACTAA   1500
```

T4 DNA Ligase CH D371T Protein

SEQ ID NO: 18

```
  1  MILKILNEIASIGSTKQKQAILEKNKDNELLKRVYRLTYSRGLQYYIKKWPKPGIATQSF    60
 61  GMLTLTDMLDFIEFTLATRKLTGNAAIEELTGYITDGKKDDVEVLRRVMMRDLECGASVS   120
121  IANKVWPGLIPEQPQMLASSYDEKGINKNIKFPAFAQLKADGARCFAEVRGDELDDVRLL   180
181  SRAGNEYLGLDLLKEELIKMTAEARQIHPEGVLIDGELVYHEQVKKEPEGLDFLFDAYPE   240
241  NSKAKEFAEVAESRTASNGIANKSLKGTISEKEAQCMKFQVWDYVPLVEIYSLPAFRLKY   300
301  DVRFSKLEQMTSGYDKVILIENQVVNNLDEAKVIYKKYIDQGLEGIILKNIDGLWENARS   360
361  KNLYKFKEVITVDLKIVGIYPHRKDPTKAGGFILESECGKIKVNAGSGLKDKAGVKSHEL   420
421  DRTRIMENQNYYIGKILECECNGWLKSDGRTDYVKLFLPIAIRLREDKTKANTFEDVFGD   480
481  FHEVTGLGSGSSGHHHHHH*                                          499
```

T4 DNA Ligase CH D371V DNA

SEQ ID NO: 19

```
  1  ATGATTCTTAAAATTCTGAACGAAATAGCATCTATTGGTTCAACTAAACAGAAGCAAGCA    60
 61  ATTCTTGAAAAGAATAAAGATAATGAATTGCTTAAACGAGTATATCGTCTGACTTATTCT   120
121  CGTGGGTTACAGTATTATATCAAGAAATGGCCTAAACCTGGTATTGCTACCCAGAGTTTT   180
181  GGAATGTTGACTCTTACCGATATGCTTGACTTCATTGAATTCACATTAGCTACTCGGAAA   240
241  TTGACTGGAAATGCAGCAATTGAGGAATTAACTGGATATATCACCGATGGTAAAAAAGAT   300
301  GATGTTGAAGTTTTGCGTCGAGTGATGATGCGAGACCTTGAATGTGGTGCTTCAGTATCT   360
361  ATTGCAAACAAAGTTTGGCCAGGTTTAATTCCTGAACAACCTCAAATGCTCGCAAGTTCT   420
421  TATGATGAAAAAGGCATTAATAAGAATATCAAATTTCCAGCCTTTGCTCAGTTAAAAGCT   480
481  GATGGAGCTCGGTGTTTTGCTGAAGTTAGAGGTGATGAATTAGATGATGTTCGTCTTTTA   540
541  TCACGAGCTGGTAATGAATATCTAGGATTAGATCTTCTTAAGGAAGAGTTAATTAAAATG   600
601  ACCGCTGAAGCCCGCCAGATTCATCCAGAAGGTGTGTTGATTGATGGCGAATTGGTATAC   660
661  CATGAGCAAGTTAAAAAGGAGCCAGAAGGCCTAGATTTTCTTTTTGATGCTTATCCTGAA   720
```

-continued

```
 721   AACAGTAAAGCTAAAGAATTCGCCGAAGTAGCTGAATCACGTACTGCTTCTAATGGAATC    780
 781   GCCAATAAATCTTTAAAGGGAACCATTTCTGAAAAAGAAGCACAATGCATGAAGTTTCAG    840
 841   GTCTGGGATTATGTCCCGTTGGTAGAAATATACAGTCTTCCTGCATTTCGTTTGAAATAT    900
 901   GATGTACGTTTTTCTAAACTAGAACAAATGACATCTGGATATGATAAAGTAATTTTAATT    960
 961   GAAAACCAGGTAGTAAATAACCTAGATGAAGCTAAGGTAATTTATAAAAAGTATATTGAC   1020
1021   CAAGGTCTTGAAGGTATTATTCTCAAAAATATCGATGGATTATGGGAAAATGCTCGTTCA   1080
1081   AAAAATCTTTATAAATTTAAAGAAGTAATTGTTGTTGATTTAAAAATTGTAGGAATTTAT   1140
1141   CCTCACCGTAAAGACCCTACTAAAGCGGGTGGATTTATTCTTGAGTCAGAGTGTGGAAAA   1200
1201   ATTAAGGTAAATGCTGGTTCAGGCTTAAAAGATAAAGCCGGTGTAAAATCGCATGAACTT   1260
1261   GACCGTACTCGCATTATGGAAAACCAAATTATTATATTGGAAAAATTCTAGAGTGCGAA    1320
1321   TGCAACGGTTGGTTAAAATCTGATGGCCGCACTGATTACGTTAAATTATTTCTTCCGATT   1380
1381   GCGATTCGTTTACGTGAAGATAAAACTAAAGCTAATACATTCGAAGATGTATTTGGTGAT   1440
1441   TTTCATGAGGTAACTGGTCTAGGTTCTGGCAGTTCAGGTCATCACCACCATCATCACTAA   1500
```

T4 DNA Ligase CH D371V Protein  
SEQ ID NO: 20

```
  1   MILKILNEIASIGSTKQKQAILEKNKDNELLKRVYRLTYSRGLQYYIKKWPKPGIATQSF    60
 61   GMLTLTDMLDFIEFTLATRKLTGNAAIEELTGYITDGKKDDVEVLRRVMMRDLECGASVS   120
121   IANKVWPGLIPEQPQMLASSYDEKGINKNIKFPAFAQLKADGARCFAEVRGDELDDVRLL   180
181   SRAGNEYLGLDLLKEELIKMTAEARQIHPEGVLIDGELVYHEQVKKEPEGLDFLFDAYPE   240
241   NSKAKEFAEVAESRTASNGIANKSLKGTISEKEAQCMKFQVWDYVPLVEIYSLPAFRLKY   300
301   DVRFSKLEQMTSGYDKVILIENQVVNNLDEAKVIYKKYIDQGLEGIILKNIDGLWENARS   360
361   KNLYKFKEVIVVDLKIVGIYPHRKDPTKAGGFILESECGKIKVNAGSGLKDKAGVKSHEL   420
421   DRTRIMENQNYYIGKILECECNGWLKSDGRTDYVKLFLPIAIRLREDKTKANTFEDVFGD   480
481   FHEVTGLGSGSSGHHHHHH*                                          499
```

T4 DNA Ligase CH D371Y DNA  
SEQ ID NO: 21

```
  1   ATGATTCTTAAAATTCTGAACGAAATAGCATCTATTGGTTCAACTAAACAGAAGCAAGCA    60
 61   ATTCTTGAAAAGAATAAAGATAATGAATTGCTTAAACGAGTATATCGTCTGACTTATTCT   120
121   CGTGGGTTACAGTATTATATCAAGAAATGGCCTAAACCTGGTATTGCTACCCAGAGTTTT   180
181   GGAATGTTGACTCTTACCGATATGCTTGACTTCATTGAATTCACATTAGCTACTCGGAAA   240
241   TTGACTGGAAATGCAGCAATTGAGGAATTAACTGGATATATCACCGATGGTAAAAAAGAT   300
301   GATGTTGAAGTTTTGCGTCGAGTGATGATGCGAGACCTTGAATGTGGTGCTTCAGTATCT   360
361   ATTGCAAACAAAGTTTGGCCAGGTTTAATTCCTGAACAACCTCAAATGCTCGCAAGTTCT   420
421   TATGATGAAAAGGCATTAATAAGAATATCAAATTTCCAGCCTTTGCTCAGTTAAAAGCT    480
481   GATGGAGCTCGGTGTTTTGCTGAAGTTAGAGGTGATGAATTAGATGATGTTCGTCTTTTA   540
541   TCACGAGCTGGTAATGAATATCTAGGATTAGATCTTCTTAAGGAAGAGTTAATTAAAATG   600
601   ACCGCTGAAGCCCGCCAGATTCATCCAGAAGGTGTGTTGATTGATGGCGAATTGGTATAC   660
661   CATGAGCAAGTTAAAAAGGAGCCAGAAGGCCTAGATTTTCTTTTTGATGCTTATCCTGAA   720
721   AACAGTAAAGCTAAAGAATTCGCCGAAGTAGCTGAATCACGTACTGCTTCTAATGGAATC   780
781   GCCAATAAATCTTTAAAGGGAACCATTTCTGAAAAAGAAGCACAATGCATGAAGTTTCAG   840
841   GTCTGGGATTATGTCCCGTTGGTAGAAATATACAGTCTTCCTGCATTTCGTTTGAAATAT   900
901   GATGTACGTTTTTCTAAACTAGAACAAATGACATCTGGATATGATAAAGTAATTTTAATT   960
961   GAAAACCAGGTAGTAAATAACCTAGATGAAGCTAAGGTAATTTATAAAAAGTATATTGAC  1020
```

-continued

```
      1021  CAAGGTCTTGAAGGTATTATTCTCAAAAATATCGATGGATTATGGGAAAATGCTCGTTCA     1080

1081  AAAAATCTTTATAAATTTAAAGAAGTAATTTACGTTGATTTAAAAATTGTAGGAATTTAT     1140

1141  CCTCACCGTAAAGACCCTACTAAAGCGGGTGGATTTATTCTTGAGTCAGAGTGTGGAAAA     1200

1201  ATTAAGGTAAATGCTGGTTCAGGCTTAAAAGATAAAGCCGGTGTAAAATCGCATGAACTT     1260

1261  GACCGTACTCGCATTATGGAAAACCAAAATTATTATATTGGAAAAATTCTAGAGTGCGAA     1320

1321  TGCAACGGTTGGTTAAAATCTGATGGCCGCACTGATTACGTTAAATTATTTCTTCCGATT     1380

1381  GCGATTCGTTTACGTGAAGATAAAACTAAAGCTAATACATTCGAAGATGTATTTGGTGAT     1440

1441  TTTCATGAGGTAACTGGTCTAGGTTCTGGCAGTTCAGGTCATCACCACCATCATCACTAA     1500
```

T4 DNA Ligase CH D371Y Protein

SEQ ID NO: 22

```
         1  MILKILNEIASIGSTKQKQAILEKNKDNELLKRVYRLTYSRGLQYYIKKWPKPGIATQSF       60

61  GMLTLTDMLDFIEFTLATRKLIGNAAIEELTGYITDGKKDDVEVLRRVMMRDLECGASVS      120

121  IANKVWPGLIPEQPQMLASSYDEKGINKNIKFPAFAQLKADGARCFAEVRGDELDDVRLL      180

181  SRAGNEYLGLDLLKEELIKMTAEARQIHPEGVLIDGELVYHEQVKKEPEGLDFLFDAYPE      240

241  NSKAKEFAEVAESRTASNGIANKSLKGTISEKEAQCMKFQVWDYVPLVEIYSLPAFRLKY      300

301  DVRFSKLEQMTSGYDKVILIENQVVNNLDEAKVIYKKYIDQGLEGIILKNIDGLWENARS      360

361  KNLYKFKEVIYVDLKIVGIYPHRKDPTKAGGFILESECGKIKVNAGSGLKDKAGVKSHEL      420

421  DRTRIMENQNYYIGKILECECNGWLKSDGRTDYVKLFLPIAIRLREDKTKANTFEDVFGD      480

481  FHEVTGLGSGSSGHHHHHH*                                             499
```

T4 DNA Ligase CH E438K DNA

SEQ ID NO: 23

```
         1  ATGATTCTTAAAATTCTGAACGAAATAGCATCTATTGGTTCAACTAAACAGAAGCAAGCA       60

61  ATTCTTGAAAAGAATAAAGATAATGAATTGCTTAAACGAGTATATCGTCTGACTTATTCT      120

121  CGTGGGTTACAGTATTATATCAAGAAATGGCCTAAACCTGGTATTGCTACCCAGAGTTTT      180

181  GGAATGTTGACTCTTACCGATATGCTTGACTTCATTGAATTCACATTAGCTACTCGGAAA      240

241  TTGACTGGAAATGCAGCAATTGAGGAATTAACTGGATATATCACCGATGGTAAAAAAGAT      300

301  GATGTTGAAGTTTTGCGTCGAGTGATGATGCGAGACCTTGAATGTGGTGCTTCAGTATCT      360

361  ATTGCAAACAAAGTTTGGCCAGGTTTAATTCCTGAACAACCTCAAATGCTCGCAAGTTCT      420

421  TATGATGAAAAGGCATTAATAAGAATATCAAATTTCCAGCCTTTGCTCAGTTAAAAGCT      480

481  GATGGAGCTCGGTGTTTTGCTGAAGTTAGAGGTGATGAATTAGATGATGTTCGTCTTTTA      540

541  TCACGAGCTGGTAATGAATATCTAGGATTAGATCTTCTTAAGGAAGAGTTAATTAAAATG      600

601  ACCGCTGAAGCCCGCCAGATTCATCCAGAAGGTGTGTTGATTGATGGCGAATTGGTATAC      660

661  CATGAGCAAGTTAAAAAGGAGCCAGAAGGCCTAGATTTTCTTTTTGATGCTTATCCTGAA      720

721  AACAGTAAAGCTAAAGAATTCGCCGAAGTAGCTGAATCACGTACTGCTTCTAATGGAATC      780

781  GCCAATAAATCTTTAAAGGGAACCATTTCTGAAAAGAAGCACAATGCATGAAGTTTCAG      840

841  GTCTGGGATTATGTCCCGTTGGTAGAAATATACAGTCTTCCTGCATTTCGTTTGAAATAT      900

901  GATGTACGTTTTTCTAAACTAGAACAAATGACATCTGGATATGATAAAGTAATTTTAATT      960

961  GAAAACCAGGTAGTAAATAACCTAGATGAAGCTAAGGTAATTTATAAAAAGTATATTGAC     1020

1021  CAAGGTCTTGAAGGTATTATTCTCAAAAATATCGATGGATTATGGGAAAATGCTCGTTCA     1080

1081  AAAAATCTTTATAAATTTAAAGAAGTAATTGATGTTGATTTAAAAATTGTAGGAATTTAT     1140

1141  CCTCACCGTAAAGACCCTACTAAAGCGGGTGGATTTATTCTTGAGTCAGAGTGTGGAAAA     1200

1201  ATTAAGGTAAATGCTGGTTCAGGCTTAAAAGATAAAGCCGGTGTAAAATCGCATGAACTT     1260
```

```
1261  GACCGTACTCGCATTATGGAAAACCAAAATTATTATATTGGAAAAATTCTAAAATGCGAA  1320
1321  TGCAACGGTTGGTTAAAATCTGATGGCCGCACTGATTACGTTAAATTATTTCTTCCGATT  1380
1381  GCGATTCGTTTACGTGAAGATAAAACTAAAGCTAATACATTCGAAGATGTATTTGGTGAT  1440
1441  TTTCATGAGGTAACTGGTCTAGGTTCTGGCAGTTCAGGTCATCACCACCATCATCACTAA  1500
```

T4 DNA Ligase CH E438K Protein

SEQ ID NO: 24

```
  1  MILKILNEIASIGSTKQKQAILEKNKDNELLKRVYRLTYSRGLQYYIKKWPKPGIATQSF   60
 61  GMLTLTDMLDFIEFTLATRKLIGNAAIEELTGYITDGKKDDVEVLRRVMMRDLECGASVS  120
121  IANKVWPGLIPEQPQMLASSYDEKGINKNIKFPAFAQLKADGARCFAEVRGDELDDVRLL  180
181  SRAGNEYLGLDLLKEELIKMTAEARQIHPEGVLIDGELVYHEQVKKEPEGLDFLFDAYPE  240
241  NSKAKEFAEVAESRTASNGIANKSLKGTISEKEAQCMKFQVWDYVPLVEIYSLPAFRLKY  300
301  DVRFSLEKQMTSGYDKVILIENQVVNNLDEAKVIYKKYIDQGLEGIILKNIDGLWENARS  360
361  KNLYKFKEVIDVDLKIVGIYPHRKDPTKAGGFILESECGKIKVNAGSGLKDKAGVKSHEL  420
421  DRTRIMENQNYYIGKILKCECNGWLKSDGRTDYVKLFLPIAIRLREDKTKANTFEDVFGD  480
481  FHEVTGLGSGSSGHHHHHH*                                          499
```

T4 DNA Ligase CH E440K DNA

SEQ ID NO: 25

```
  1  ATGATTCTTAAAATTCTGAACGAAATAGCATCTATTGGTTCAACTAAACAGAAGCAAGCA   60
 61  ATTCTTGAAAAGAATAAAGATAATGAATTGCTTAAACGAGTATATCGTCTGACTTATTCT  120
121  CGTGGGTTACAGTATTATATCAAGAAATGGCCTAAACCTGGTATTGCTACCCAGAGTTTT  180
181  GGAATGTTGACTCTTACCGATATGCTTGACTTCATTGAATTCACATTAGCTACTCGGAAA  240
241  TTGACTGGAAATGCAGCAATTGAGGAATTAACTGGATATATCACCGATGGTAAAAAGAT  300
301  GATGTTGAAGTTTTGCGTCGAGTGATGATGCGAGACCTTGAATGTGGTGCTTCAGTATCT  360
361  ATTGCAAACAAAGTTTGGCCAGGTTTAATTCCTGAACAACCTCAAATGCTCGCAAGTTCT  420
421  TATGATGAAAAGGCATTAATAAGAATATCAAATTTCCAGCCTTTGCTCAGTTAAAAGCT  480
481  GATGGAGCTCGGTGTTTTGCTGAAGTTAGAGGTGATGAATTAGATGATGTTCGTCTTTTA  540
541  TCACGAGCTGGTAATGAATATCTAGGATTAGATCTTCTTAAGGAAGAGTTAATTAAATG  600
601  ACCGCTGAAGCCCGCCAGATTCATCCAGAAGGTGTGTTGATTGATGGCGAATTGGTATAC  660
661  CATGAGCAAGTTAAAAAGGAGCCAGAAGGCCTAGATTTTCTTTTTGATGCTTATCCTGAA  720
721  AACAGTAAAGCTAAAGAATTCGCCGAAGTAGCTGAATCACGTACTGCTTCTAATGGAATC  780
781  GCCAATAAATCTTTAAAGGGAACCATTTCTGAAAAAGAAGCACAATGCATGAAGTTTCAG  840
841  GTCTGGGATTATGTCCCGTTGGTAGAAATATACAGTCTTCCTGCATTTCGTTTGAAATAT  900
901  GATGTACGTTTTTCTAAACTAGAACAAATGACATCTGGATATGATAAAGTAATTTTAATT  960
961  GAAAACCAGGTAGTAAATAACCTAGATGAAGCTAAGGTAATTTATAAAAAGTATATTGAC 1020
1021  CAAGGTCTTGAAGGTATTATTCTCAAAAATATCGATGGATTATGGGAAAATGCTCGTTCA 1080
1081  AAAAATCTTTATAAATTTAAAGAAGTAATTGATGTTGATTTAAAAATTGTAGGAATTTAT 1140
1141  CCTCACCGTAAAGACCCTACTAAAGCGGGTGGATTTATTCTTGAGTCAGAGTGTGGAAAA 1200
1201  ATTAAGGTAAATGCTGGTTCAGGCTTAAAAGATAAAGCCGGTGTAAAATCGCATGAACTT 1260
1261  GACCGTACTCGCATTATGGAAAACCAAAATTATTATATTGGAAAAATTCTAGAGTGCAAA 1320
1321  TGCAACGGTTGGTTAAAATCTGATGGCCGCACTGATTACGTTAAATTATTTCTTCCGATT 1380
1381  GCGATTCGTTTACGTGAAGATAAAACTAAAGCTAATACATTCGAAGATGTATTTGGTGAT 1440
1441  TTTCATGAGGTAACTGGTCTAGGTTCTGGCAGTTCAGGTCATCACCACCATCATCACTAA 1500
```

T4 DNA Ligase CH E440K Protein
SEQ ID NO: 26
```
  1  MILKILNEIASIGSTKQKQAILEKNKDNELLKRVYRLTYSRGLQYYIKKWPKPGIATQSF     60
 61  GMLTLTDMLDFIEFTLATRKLIGNAAIEELTGYITDGKKDDVEVLRRVMMRDLECGASVS    120
121  IANKVWPGLIPEQPQMLASSYDEKGINKNIKFPAFAQLKADGARCFAEVRGDELDDVRLL    180
181  SRAGNEYLGLDLLKEELIKMTAEARQIHPEGVLIDGELVYHEQVKKEPEGLDFLFDAYPE    240
241  NSKAKEFAEVAESRTASNGIANKSLKGTISEKEAQCMKFQVWDYVPLVEIYSLPAFRLKY    300
301  DVRFSKLEQMTSGYDKVILIENQVVNNLDEAKVIYKKYIDQGLEGIILKNIDGLWENARS    360
361  KNLYKFKEVIDVDLKIVGIYPHRKDPTKAGGFILESECGKIKVNAGSGLKDKAGVKSHEL    420
421  DRTRIMENQNYYIGKILECKCNGWLKSDGRTDYVKLFLPIAIRLREDKTKANTFEDVFGD    480
481  FHEVTGLGSGSSGHHHHHH*                                           499
```

T4 DNA Ligase CH E440R DNA
SEQ ID NO: 27
```
   1  ATGATTCTTAAAATTCTGAACGAAATAGCATCTATTGGTTCAACTAAACAGAAGCAAGCA     60
  61  ATTCTTGAAAAGAATAAAGATAATGAATTGCTTAAACGAGTATATCGTCTGACTTATTCT    120
 121  CGTGGGTTACAGTATTATATCAAGAAATGGCCTAAACCTGGTATTGCTACCCAGAGTTTT    180
 181  GGAATGTTGACTCTTACCGATATGCTTGACTTCATTGAATTCACATTAGCTACTCGGAAA    240
 241  TTGACTGGAAATGCAGCAATTGAGGAATTAACTGGATATATCACCGATGGTAAAAAAGAT    300
 301  GATGTTGAAGTTTTGCGTCGAGTGATGATGCGAGACCTTGAATGTGGTGCTTCAGTATCT    360
 361  ATTGCAAACAAAGTTTGGCCAGGTTTAATTCCTGAACAACCTCAAATGCTCGCAAGTTCT    420
 421  TATGATGAAAAAGGCATTAATAAGAATATCAAATTTCCAGCCTTTGCTCAGTTAAAAGCT    480
 481  GATGGAGCTCGGTGTTTTGCTGAAGTTAGAGGTGATGAATTAGATGATGTTCGTCTTTTA    540
 541  TCACGAGCTGGTAATGAATATCTAGGATTAGATCTTCTTAAGGAAGAGTTAATTAAAATG    600
 601  ACCGCTGAAGCCCGCCAGATTCATCCAGAAGGTGTGTTGATTGATGGCGAATTGGTATAC    660
 661  CATGAGCAAGTTAAAAAGGAGCCAGAAGGCCTAGATTTTCTTTTTGATGCTTATCCTGAA    720
 721  AACAGTAAAGCTAAAGAATTCGCCGAAGTAGCTGAATCACGTACTGCTTCTAATGGAATC    780
 781  GCCAATAAATCTTTAAAGGGAACCATTTCTGAAAAAGAAGCACAATGCATGAAGTTTCAG    840
 841  GTCTGGGATTATGTCCCGTTGGTAGAAATATACAGTCTTCCTGCATTTCGTTTGAAATAT    900
 901  GATGTACGTTTTTCTAAACTAGAACAAATGACATCTGGATATGATAAAGTAATTTTAATT    960
 961  GAAAACCAGGTAGTAAATAACCTAGATGAAGCTAAGGTAATTTATAAAAAGTATATTGAC   1020
1021  CAAGGTCTTGAAGGTATTATTCTCAAAAATATCGATGGATTATGGGAAAATGCTCGTTCA   1080
1081  AAAAATCTTTATAAATTTAAAGAAGTAATTGATGTTGATTTAAAAATTGTAGGAATTTAT   1140
1141  CCTCACCGTAAAGACCCTACTAAAGCGGGTGGATTTATTCTTGAGTCAGAGTGTGGAAAA   1200
1201  ATTAAGGTAAATGCTGGTTCAGGCTTAAAAGATAAAGCCGGTGTAAAATCGCATGAACTT   1260
1261  GACCGTACTCGCATTATGGAAAACCAAAATTATTATATTGGAAAAATTCTAGAGTGCCGT   1320
1321  TGCAACGGTTGGTTAAAATCTGATGGCCGCACTGATTACGTTAAATTATTTCTTCCGATT   1380
1381  GCGATTCGTTTACGTGAAGATAAAACTAAAGCTAATACATTCGAAGATGTATTTGGTGAT   1440
1441  TTTCATGAGGTAACTGGTCTAGGTTCTGGCAGTTCAGGTCATCACCACCATCATCACTAA   1500
```

T4 DNA Ligase CH E440R Protein
SEQ ID NO: 28
```
  1  MILKILNEIASIGSTKQKQAILEKNKDNELLKRVYRLTYSRGLQYYIKKWPKPGIATQSF     60
 61  GMLTLTDMLDFIEFTLATRKLTGNAAIEELTGYITDGKKDDVEVLRRVMMRDLECGASVS    120
121  IANKVWPGLIPEQPQMLASSYDEKGINKNIKFPAFAQLKADGARCFAEVRGDELDDVRLL    180
```

-continued

```
  181   SRAGNEYLGLDLLKEELIKMTAEARQIHPEGVLIDGELVYHEQVKKEPEGLDFLFDAYPE    240
  241   NSKAKEFAEVAESRTASNGIANKSLKGTISEKEAQCMKFQVWDYVPLVEIYSLPAFRLKY    300
  301   DVRFSKLEQMTSGYDKVILIENQVVNNLDEAKVIYKKYIDQGLEGIILKNIDGLWENARS    360
  361   KNLYKFKEVIDVDLKIVGIYPHRKDPTKAGGFILESECGKIKVNAGSGLKDKAGVKSHEL    420
  421   DRTRIMENQNYYIGKILECRCNGWLKSDGRTDYVKLFLPIAIRLREDKTKANTFEDVFGD    480
  481   FHEVTGLGSGSSGHHHHHH*                                           499
```

T4 DNA Ligase CH E440S DNA

SEQ ID NO: 29

```
    1   ATGATTCTTAAAATTCTGAACGAAATAGCATCTATTGGTTCAACTAAACAGAAGCAAGCA    60
   61   ATTCTTGAAAAGAATAAAGATAATGAATTGCTTAAACGAGTATATCGTCTGACTTATTCT   120
  121   CGTGGGTTACAGTATTATATCAAGAAATGGCCTAAACCTGGTATTGCTACCCAGAGTTTT   180
  181   GGAATGTTGACTCTTACCGATATGCTTGACTTCATTGAATTCACATTAGCTACTCGGAAA   240
  241   TTGACTGGAAATGCAGCAATTGAGGAATTAACTGGATATATCACCGATGGTAAAAAAGAT   300
  301   GATGTTGAAGTTTTGCGTCGAGTGATGATGCGAGACCTTGAATGTGGTGCTTCAGTATCT   360
  361   ATTGCAAACAAAGTTTGGCCAGGTTTAATTCCTGAACAACCTCAAATGCTCGCAAGTTCT   420
  421   TATGATGAAAAGGCATTAATAAGAATATCAAATTTCCAGCCTTTGCTCAGTTAAAAGCT   480
  481   GATGGAGCTCGGTGTTTTGCTGAAGTTAGAGGTGATGAATTAGATGATGTTCGTCTTTTA   540
  541   TCACGAGCTGGTAATGAATATCTAGGATTAGATCTTCTTAAGGAAGAGTTAATTAAAATG   600
  601   ACCGCTGAAGCCCGCCAGATTCATCCAGAAGGTGTGTTGATTGATGGCGAATTGGTATAC   660
  661   CATGAGCAAGTTAAAAAGGAGCCAGAAGGCCTAGATTTTCTTTTTGATGCTTATCCTGAA   720
  721   AACAGTAAAGCTAAAGAATTCGCCGAAGTAGCTGAATCACGTACTGCTTCTAATGGAATC   780
  781   GCCAATAAATCTTTAAAGGGAACCATTTCTGAAAAAGAAGCACAATGCATGAAGTTTCAG   840
  841   GTCTGGGATTATGTCCCGTTGGTAGAAATATACAGTCTTCCTGCATTTCGTTTGAAATAT   900
  901   GATGTACGTTTTTCTAAACTAGAACAAATGACATCTGGATATGATAAAGTAATTTTAATT   960
  961   GAAAACCAGGTAGTAAATAACCTAGATGAAGCTAAGGTAATTTATAAAAAGTATATTGAC   1020
 1021   CAAGGTCTTGAAGGTATTATTCTCAAAAATATCGATGGATTATGGGAAAATGCTCGTTCA   1080
 1081   AAAAATCTTTATAAATTTAAAGAAGTAATTGATGTTGATTTAAAAATTGTAGGAATTTAT   1140
 1141   CCTCACCGTAAAGACCCTACTAAAGCGGGTGGATTTATTCTTGAGTCAGAGTGTGGAAAA   1200
 1201   ATTAAGGTAAATGCTGGTTCAGGCTTAAAAGATAAGCCGGTGTAAAATCGCATGAACTT   1260
 1261   GACCGTACTCGCATTATGGAAAACCAAAATTATTATATTGGAAAAATTCTAGAGTGCTCT   1320
 1321   TGCAACGGTTGGTAAAATCTGATGGCCGCACTGATTACGTTAAATTATTTCTTCCGATT   1380
 1381   GCGATTCGTTTACGTGAAGATAAAACTAAAGCTAATACATTCGAAGATGTATTTGGTGAT   1440
 1441   TTTCATGAGGTAACTGGTCTAGGTTCTGGCAGTTCAGGTCATCACCACCATCATCACTAA   1500
```

T4 DNA Ligase CH E440S Protein

SEQ ID NO: 30

```
    1   MILKILNEIASIGSTKQKQAILEKNKDNELLKRVYRLTYSRGLQYYIKKWPKPGIATQSF    60
   61   GMLTLTDMLDFIEFTLATRKLIGNAAIEELTGYITDGKKDDVEVLRRVMMRDLECGASVS   120
  121   IANKVWPGLIPEQPQMLASSYDEKGINKNIKFPAFAQLKADGARCFAEVRGDELDDVRLL   180
  181   SRAGNEYLGLDLLKEELIKMTAEARQIHPEGVLIDGELVYHEQVKKEPEGLDFLFDAYPE   240
  241   NSKAKEFAEVAESRTASNGIANKSLKGTISEKEAQCMKFQVWDYVPLVEIYSLPAFRLKY   300
  301   DVRFSKLEQMTSGYDKVILIENQVVNNLDEAKVIYKKYIDQGLEGIILKNIDGLWENARS   360
```

```
    361  KNLYKFKEVIDVDLKIVGIYPHRKDPTKAGGFILESECGKIKVNAGSLKDKAGVKSHEL        420
    421  DRTRIMENQNYYIGKILECSCNGWLKSDGRTDYVKLFLPIAIRLREDKTKANTFEDVFGD        480
    481  FHEVTGLGSGSSGHHHHHH*                                                499
```

T4 DNA Ligase CH E466K DNA

SEQ ID NO: 31

```
      1  ATGATTCTTAAAATTCTGAACGAAATAGCATCTATTGGTTCAACTAAACAGAAGCAAGCA        60
     61  ATTCTTGAAAAGAATAAAGATAATGAATTGCTTAAACGAGTATATCGTCTGACTTATTCT       120
    121  CGTGGGTTACAGTATTATATCAAGAAATGGCCTAAACCTGGTATTGCTACCCAGAGTTTT       180
    181  GGAATGTTGACTCTTACCGATATGCTTGACTTCATTGAATTCACATTAGCTACTCGGAAA       240
    241  TTGACTGGAAATGCAGCAATTGAGGAATTAACTGGATATATCACCGATGGTAAAAAGAT       300
    301  GATGTTGAAGTTTTGCGTCGAGTGATGATGCGAGACCTTGAATGTGGTGCTTCAGTATCT       360
    361  ATTGCAAACAAAGTTTGGCCAGGTTTAATTCCTGAACAACCTCAAATGCTCGCAAGTTCT       420
    421  TATGATGAAAAGGCATTAATAAGAATATCAAATTTCCAGCCTTTGCTCAGTTAAAAGCT        480
    481  GATGGAGCTCGGTGTTTTGCTGAAGTTAGAGGTGATGAATTAGATGATGTTCGTCTTTTA       540
    541  TCACGAGCTGGTAATGAATATCTAGGATTAGATCTTCTTAAGGAAGAGTTAATTAAAATG       600
    601  ACCGCTGAAGCCCGCCAGATTCATCCAGAAGGTGTGTTGATTGATGGCGAATTGGTATAC       660
    661  CATGAGCAAGTTAAAAAGGAGCCAGAAGGCCTAGATTTTCTTTTTGATGCTTATCCTGAA       720
    721  AACAGTAAAGCTAAAGAATTCGCCGAAGTAGCTGAATCACGTACTGCTTCTAATGGAATC       780
    781  GCCAATAAATCTTTAAAGGGAACCATTTCTGAAAAAGAAGCACAATGCATGAAGTTTCAG       840
    841  GTCTGGGATTATGTCCCGTTGGTAGAAATATACAGTCTTCCTGCATTTCGTTTGAAATAT       900
    901  GATGTACGTTTTTCTAAACTAGAACAAATGACATCTGGATATGATAAAGTAATTTTAATT       960
    961  GAAAACCAGGTAGTAAATAACCTAGATGAAGCTAAGGTAATTTATAAAAAGTATATTGAC      1020
   1021  CAAGGTCTTGAAGGTATTATTCTCAAAAATATCGATGGATTATGGGAAAATGCTCGTTCA      1080
   1081  AAAAATCTTTATAAATTTAAAGAAGTAATTGATGTTGATTTAAAAATTGTAGGAATTTAT      1140
   1141  CCTCACCGTAAAGACCCTACTAAAGCGGGTGGATTTATTCTTGAGTCAGAGTGTGGAAAA      1200
   1201  ATTAAGGTAAATGCTGGTTCAGGCTTAAAAGATAAAGCCGGTGTAAAATCGCATGAACTT      1260
   1261  GACCGTACTCGCATTATGGAAAACCAAAATTATTATATTGGAAAAATTCTAGAGTGCGAA      1320
   1321  TGCAACGGTTGGTAAAATCTGATGGCCGCACTGATTACGTTAAATTATTTCTTCCGATT       1380
   1381  GCGATTCGTTTACGTAAAGATAAAACTAAAGCTAATACATTCGAAGATGTATTTGGTGAT      1440
   1441  TTTCATGAGGTAACTGGTCTAGGTTCTGGCAGTTCAGGTCATCACCACCATCATCACTAA      1500
```

T4 DNA Ligase CH E466K Protein

SEQ ID NO: 32

```
      1  MILKILNEIASIGSTKQKQAILEKNKDNELLKRVYRLTYSRGLQYYIKKWPKPGIATQSF        60
     61  GMLTLTDMLDFIEFTLATRKLIGNAAIEELTGYITDGKKDDVEVLRRVMMRDLECGASVS       120
    121  IANKVWPGLIPEQPQMLASSYDEKGINKNIKFPAFAQLKADGARCFAEVRGDELDDVRLL       180
    181  SRAGNEYLGLDLLKEELIKMTAEARQIHPEGVLIDGELVYHEQVKKEPEGLDFLFDAYPE       240
    241  NSKAKEFAEVAESRTASNGIANKSLKGTISEKEAQCMKFQVWDYVPLVEIYSLPAFRLKY       300
    301  DVRFSKLEQMTSGYDKVILIENQVVNNLDEAKVIYKKYIDQGLEGIILKNIDGLWENARS       360
    361  KNLYKFKEVIDVDLKIVGIYPHRKDPTKAGGFILESECGKIKVNAGSLKDKAGVKSHEL        420
    421  DRTRIMENQNYYIGKILECECNGWLKSDGRTDYVKLFLPIAIRLRKDKTKANTFEDVFGD       480
    481  FHEVTGLGSGSSGHHHHHH*                                                499
```

-continued

T4 DNA Ligase CH E483K DNA

SEQ ID NO: 33

```
   1  ATGATTCTTAAAATTCTGAACGAAATAGCATCTATTGGTTCAACTAAACAGAAGCAAGCA    60
  61  ATTCTTGAAAAGAATAAAGATAATGAATTGCTTAAACGAGTATATCGTCTGACTTATTCT   120
 121  CGTGGGTTACAGTATTATATCAAGAAATGGCCTAAACCTGGTATTGCTACCCAGAGTTTT   180
 181  GGAATGTTGACTCTTACCGATATGCTTGACTTCATTGAATTCACATTAGCTACTCGGAAA   240
 241  TTGACTGGAAATGCAGCAATTGAGGAATTAACTGGATATATCACCGATGGTAAAAAAGAT   300
 301  GATGTTGAAGTTTTGCGTCGAGTGATGATGCGAGACCTTGAATGTGGTGCTTCAGTATCT   360
 361  ATTGCAAACAAAGTTTGGCCAGGTTTAATTCCTGAACAACCTCAAATGCTCGCAAGTTCT   420
 421  TATGATGAAAAAGGCATTAATAAGAATATCAAATTTCCAGCCTTTGCTCAGTTAAAAGCT   480
 481  GATGGAGCTCGGTGTTTTGCTGAAGTTAGAGGTGATGAATTAGATGATGTTCGTCTTTTA   540
 541  TCACGAGCTGGTAATGAATATCTAGGATTAGATCTTCTTAAGGAAGAGTTAATTAAAATG   600
 601  ACCGCTGAAGCCCGCCAGATTCATCCAGAAGGTGTGTTGATTGATGGCGAATTGGTATAC   660
 661  CATGAGCAAGTTAAAAAGGAGCCAGAAGGCCTAGATTTTCTTTTTGATGCTTATCCTGAA   720
 721  AACAGTAAAGCTAAAGAATTCGCCGAAGTAGCTGAATCACGTACTGCTTCTAATGGAATC   780
 781  GCCAATAAATCTTTAAAGGGAACCATTTCTGAAAAAGAAGCACAATGCATGAAGTTTCAG   840
 841  GTCTGGGATTATGTCCCGTTGGTAGAAATATACAGTCTTCCTGCATTTCGTTTGAAATAT   900
 901  GATGTACGTTTTTCTAAACTAGAACAAATGACATCTGGATATGATAAAGTAATTTTAATT   960
 961  GAAAACCAGGTAGTAAATAACCTAGATGAAGCTAAGGTAATTTATAAAAAGTATATTGAC  1020
1021  CAAGGTCTTGAAGGTATTATTCTCAAAAATATCGATGGATTATGGGAAAATGCTCGTTCA  1080
1081  AAAAATCTTTATAAATTTAAAGAAGTAATTGATGTTGATTTAAAAATTGTAGGAATTTAT  1140
1141  CCTCACCGTAAAGACCCTACTAAAGCGGGTGGATTTATTCTTGAGTCAGAGTGTGGAAAA  1200
1201  ATTAAGGTAAATGCTGGTTCAGGCTTAAAAGATAAAGCCGGTGTAAAATCGCATGAACTT  1260
1261  GACCGTACTCGCATTATGGAAAACCAAAATTATTATATTGGAAAAATTCTAGAGTGCGAA  1320
1321  TGCAACGGTTGGTTAAAATCTGATGGCCGCACTGATTACGTTAAATTATTTCTTCCGATT  1380
1381  GCGATTCGTTTACGTGAAGATAAAACTAAAGCTAATACATTCGAAGATGTATTTGGTGAT  1440
1441  TTTCATAAAGTAACTGGTCTAGGTTCTGGCAGTTCAGGTCATCACCACCATCATCACTAA  1500
```

T4 DNA Ligase CH E483K Protein

SEQ ID NO: 34

```
  1  MILKILNEIASIGSTKQKQAILEKNKDNELLKRVYRLTYSRGLQYYIKKWPKPGIATQSF    60
 61  GMLTLTDMLDFIEFTLATRKLIGNAAIEELTGYITDGKKDDVEVLRRVMMRDLECGASVS   120
121  IANKVWPGLIPEQPQMLASSYDEKGINKNIKFPAFAQLKADGARCFAEVRGDELDDVRLL   180
181  SRAGNEYLGLDLLKEELIKMTAEARQIHPEGVLIDGELVYHEQVKKEPEGLDFLFDAYPE   240
241  NSKAKEFAEVAESRTASNGIANKSLKGTISEKEAQCMKFQVWDYVPLVEIYSLPAFRLKY   300
301  DVRFSKLEQMTSGYDKVILIENQVVNNLDEAKVIYKKYIDQGLEGIILKNIDGLWENARS   360
361  KNLYKFKEVIDVDLKIVGIYPHRKDPTKAGGFILESECGKIKVNAGSGLKDKAGVKSHEL   420
421  DRTRIMENQNYYIGKILECECNGWLKSDGRTDYVKLFLPIAIRLREDKTKANTFEDVFGD   480
481  FHKVTGLGSGSSGHHHHHH*                                          499
```

What is claimed is:

1. A mutant T4 DNA ligase, comprising the amino acid sequence of SEQ ID NO:6 from amino acid numbers 1 to 487.

2. A process of conducting polynucleotide ligation between different polynucleotides or by ligating the 5' and 3' ends of polynucleotides to generate circular polynucleotide, wherein the polynucleotides have blunt ends or cohesive ends, comprising:
   providing a ligation mixture including the polynucleotides to be ligated and a mutant T4 DNA ligase or a biologically active fragment of claim 1; and
   providing a reaction temperature greater than 37° C. for the ligation mixture.

3. The process of claim 2 wherein the reaction temperature is greater than 42° C.

4. The process of claim 2 wherein the ligation reaction mixture includes Tris-HCl, MgCl$_2$, ATP, dithiothreitol and water.

5. A mutant T4 DNA ligase having the sequence of SEQ ID NO:6.

* * * * *

SEQUENCE LISTING

<160> NUMBER OF SEQ ID NOS: 35

<210> SEQ ID NO 1
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca agtttggcc aggtttaatt cctgaacaac ctcaaatgct cgcaagttct     420
tatgatgaaa aaggcattaa taagaatatc aaatttccag cctttgctca gttaaaagct     480
gatggagctc ggtgttttgc tgaagttaga ggtgatgaat tagatgatgt tcgtcttta      540
tcacgagctg gtaatgaata tctaggatta gatcttctta aggaagagtt aattaaaatg     600
accgctgaag cccgccagat tcatccagaa ggtgtgttga ttgatggcga attggtatac     660
catgagcaag ttaaaaagga gccagaaggc ctagattttc ttttgatgc ttatcctgaa      720
aacagtaaag ctaagaatt cgccgaagta gctgaatcac gtactgcttc taatggaatc     780
gccaataaat ctttaaaggg aaccatttct gaaaaagaag cacaatgcat gaagtttcag     840
gtctgggatt atgtcccgtt ggtagaaata tacagtcttc ctgcatttcg tttgaaatat     900
gatgtacgtt tttctaaact agaacaaatg acatctggat atgataaagt aattttaatt     960
gaaaaccagg tagtaaataa cctagatgaa gctaaggtaa tttataaaaa gtatattgac    1020
caaggtcttg aaggtattat tctcaaaat atcgatggat atgggaaaa tgctcgttca     1080
aaaaatcttt ataaatttaa agaagtaatt gatgttgatt taaaaattgt aggaatttat    1140
cctcaccgta aagaccctac taaagcgggt ggatttattc ttgagtcaga gtgtggaaaa    1200
attaaggtaa atgctggttc aggcttaaaa gataaagccg gtgtaaaatc gcatgaactt    1260
gaccgtactc gcattatgga aaaccaaaat tattatattg gaaaaattct agagtgcgaa    1320
tgcaacggtt ggttaaaatc tgatggccgc actgattacg ttaaattatt tcttccgatt    1380
gcgattcgtt tacgtgaaga taaaactaaa gctaatacat cgaagatgt atttggtgat     1440
tttcatgagg taactggtct aggttctggc agttcaggtc atcaccacca tcatcactaa    1500
```

<210> SEQ ID NO 2
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30
```

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
 50                  55                  60

Leu Thr Asp Met Leu Asp Phe Ile Glu Phe Thr Leu Ala Thr Arg Lys
 65                  70                  75                  80

Leu Thr Gly Asn Ala Ala Ile Glu Glu Leu Thr Gly Tyr Ile Thr Asp
                 85                  90                  95

Gly Lys Lys Asp Asp Val Glu Val Leu Arg Arg Val Met Met Arg Asp
                100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
            130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
            195                 200                 205

Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
            275                 280                 285

Glu Ile Tyr Ser Leu Pro Ala Phe Arg Leu Lys Tyr Asp Val Arg Phe
            290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
            355                 360                 365

Val Ile Asp Val Asp Leu Lys Ile Val Gly Ile Tyr Pro His Arg Lys
            370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
            435                 440                 445

```
Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Ser Gly His His His
                485                 490                 495

His His His
```

```
<210> SEQ ID NO 3
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca agtttggcc aggtttaatt cctaaacaac tcaaatgct cgcaagttct       420 tatgatgaaa aaggcattaa taagaatatc aaatttccag cctttgctca gttaaaagct     480
gatggagctc ggtgttttgc tgaagttaga ggtgatgaat tagatgatgt tcgtcttta     540 tcacgagctg gtaatgaata tctaggatta gatcttctta aggaagagtt aattaaaatg     600
accgctgaag cccgccagat tcatccagaa ggtgtgttga ttgatggcga attggtatac     660
catgagcaag ttaaaaagga gccagaaggc ctagattttc ttttttgatgc ttatcctgaa     720 aacagtaaag ctaaagaatt cgccgaagta gctgaatcac gtactgcttc taatggaatc     780
gccaataaat ctttaaaggg aaccatttct gaaaaagaag cacaatgcat gaagtttcag     840
gtctgggatt atgtcccgtt ggtagaaata tacagtcttc ctgcatttcg tttgaaatat     900
gatgtacgtt tttctaaact agaacaaatg acatctggat atgataaagt aattttaatt     960
gaaaaccagg tagtaaataa cctagatgaa gctaaggtaa tttataaaaa gtatattgac    1020
caaggtcttg aaggtattat tctcaaaaat atcgatggat tatgggaaaa tgctcgttca    1080
aaaaatcttt ataaatttaa agaagtaatt gatgttgatt taaaaattgt aggaatttat    1140
cctcaccgta aagaccctac taaagcgggt ggatttattc ttgagtcaga gtgtggaaaa    1200
attaaggtaa atgctggttc aggcttaaaa gataaagccg gtgtaaaatc gcatgaactt    1260
gaccgtactc gcattatgga aaaccaaaat tattatattg gaaaaattct agagtgcgaa    1320
tgcaacggtt ggttaaaatc tgatggccgc actgattacg ttaaattatt tcttccgatt    1380
gcgattcgtt tacgtgaaga taaaactaaa gctaatacat cgaagatgt atttggtgat     1440 tttcatgagg taactggtct aggttctggc agttcaggtc atcaccacca tcatcactaa    1500
```

```
<210> SEQ ID NO 4
<211> LENGTH: 499
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 4

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Lys Gln Pro Gln Met Leu Ala Ser Ser Tyr Asp Glu Lys
130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
370                 375                 380
```

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
            405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Ser Gly His His His
                485                 490                 495

His His His

<210> SEQ ID NO 5
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgattctta aaattctgaa cgaaatagca tctattggtt caactaaaca gaagcaagca    60
attcttgaaa agaataaaga taatgaattg cttaaacgag tatatcgtct gacttattct   120
cgtgggttac agtattatat caagaaatgg cctaaacctg gtattgctac ccagagtttt   180
ggaatgttga ctcttaccga tatgcttgac ttcattgaat tcacattagc tactcggaaa   240
ttgactggaa atgcagcaat tgaggaatta actggatata tcaccgatgg taaaaaagat   300
gatgttgaag ttttgcgtcg agtgatgatg cgagaccttg aatgtggtgc ttcagtatct   360
attgcaaaca agtttggcc aggtttaatt cctgaacaac ctcaaatgct cgcaagttct   420
tatgatgaaa aaggcattaa taagaatatc aaatttccag cctttgctca gttaaaagct   480
gatggagctc ggtgttttgc tgaagttaga ggtgatgaat tagatgatgt tcgtctttta   540
tcacgagctg gtaatgaata tctaggatta gatcttctta aggaagagtt aattaaaatg   600
accgctgaag cccgccagat tcatccagaa ggtgtgttga ttgatggcga attggtatac   660
catgagcaag ttaaaaagga gccagaaggc ctagattttc tttttgatgc ttatcctgaa   720
aacagtaaag ctaaagaatt cgccgaagta gctgaatcac gtactgcttc taatggaatc   780
gccaataaat ctttaaaggg aaccatttct gaaaaagaag cacaatgcat gaagtttcag   840
gtctgggatt atgtcccgtt ggtagaaata tacagtcttc ctgcatttcg tttgaaatat   900
gatgtacgtt tttctaaact agaacaaatg acatctggat atgataaagt aatttttaatt   960 gaaaaccagg tagtaaataa cctagatgaa gctaaggtaa tttataaaaa gtatattgac  1020
caaggtcttg aaggtattat tctcaaaaat atcgatggat tatgggaaaa tgctcgttca  1080
aaaaatcttt ataaatttaa agaagtaatt gcagttgatt taaaaattgt aggaatttat  1140
cctcaccgta agaccctac taaagcgggt ggatttattc ttgagtcaga gtgtggaaaa  1200
attaaggtaa atgctggttc aggcttaaaa gataaagccg gtgtaaaatc gcatgaactt  1260
gaccgtactc gcattatgga aaaccaaaat tattatattg gaaaaattct agagtgcgaa  1320

```
tgcaacggtt ggttaaaatc tgatggccgc actgattacg ttaaattatt tcttccgatt    1380
gcgattcgtt tacgtgaaga taaaactaaa gctaatacat tcgaagatgt atttggtgat    1440
tttcatgagg taactggtct aggttctggc agttcaggtc atcaccacca tcatcactaa    1500
```

<210> SEQ ID NO 6
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335
```

```
Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Glu
            355                 360                 365

Val Ile Ala Val Asp Leu Lys Ile Val Gly Ile Tyr Pro His Arg Lys
        370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Ser Gly His His His
                485                 490                 495

His His His

<210> SEQ ID NO 7
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca aagtttggcc aggtttaatt cctgaacaac tcaaatgct cgcaagttct     420 tatgatgaaa aaggcattaa taagaatatc aaatttccag cctttgctca gttaaaagct     480
gatggagctc ggtgttttgc tgaagttaga ggtgatgaat tagatgatgt tcgtctttta     540
tcacgagctg gtaatgaata tctaggatta gatcttctta aggaagagtt aattaaaatg     600
accgctgaag cccgccagat tcatccagaa ggtgtgttga ttgatggcga attggtatac     660
catgagcaag ttaaaaagga gccagaaggc ctagattttc ttttttgatgc ttatcctgaa     720 aacagtaaag ctaagaatt cgccgaagta gctgaatcac gtactgcttc taatggaatc     780
gccaataaat ctttaaaggg aaccatttct gaaaagaag cacaatgcat gaagtttcag     840
gtctgggatt atgtcccgtt ggtagaaata tacagtcttc ctgcatttcg tttgaaatat     900
gatgtacgtt tttctaaact agaacaaatg acatctggat atgataaagt aattttaatt     960 gaaaccagg tagtaaataa cctagatgaa gctaaggtaa tttataaaaa gtatattgac    1020
caaggtcttg aagtattat tctcaaaaat atcgatggat tatgggaaaa tgctcgttca    1080
```

-continued

```
aaaaatcttt ataaatttaa agaagtaatt catgttgatt taaaaattgt aggaatttat    1140
cctcaccgta aagaccctac taaagcgggt ggatttattc ttgagtcaga gtgtggaaaa    1200
attaaggtaa atgctggttc aggcttaaaa gataaagccg gtgtaaaatc gcatgaactt    1260
gaccgtactc gcattatgga aaaccaaaat tattatattg gaaaaattct agagtgcgaa    1320
tgcaacggtt ggttaaaatc tgatggccgc actgattacg ttaaattatt tcttccgatt    1380
gcgattcgtt tacgtgaaga taaaactaaa gctaatacat tcgaagatgt atttggtgat    1440
tttcatgagg taactggtct aggttctggc agttcaggtc atcaccacca tcatcactaa    1500
```

<210> SEQ ID NO 8
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285
```

```
Glu Ile Tyr Ser Leu Pro Ala Phe Arg Leu Lys Tyr Asp Val Arg Phe
    290                 295                 300
Ser Lys Leu Glu Gln Met Thr Ser Gly Tyr Asp Lys Val Ile Leu Ile
305                 310                 315                 320
Glu Asn Gln Val Val Asn Asn Leu Asp Glu Ala Lys Val Ile Tyr Lys
                325                 330                 335
Lys Tyr Ile Asp Gln Gly Leu Glu Gly Ile Ile Leu Lys Asn Ile Asp
            340                 345                 350
Gly Leu Trp Glu Asn Ala Arg Ser Lys Asn Leu Tyr Lys Phe Lys Glu
        355                 360                 365
Val Ile His Val Asp Leu Lys Ile Val Gly Ile Tyr Pro His Arg Lys
    370                 375                 380
Asp Pro Thr Lys Ala Gly Gly Phe Ile Leu Glu Ser Glu Cys Gly Lys
385                 390                 395                 400
Ile Lys Val Asn Ala Gly Ser Gly Leu Lys Asp Lys Ala Gly Val Lys
                405                 410                 415
Ser His Glu Leu Asp Arg Thr Arg Ile Met Glu Asn Gln Asn Tyr Tyr
            420                 425                 430
Ile Gly Lys Ile Leu Glu Cys Glu Cys Asn Gly Trp Leu Lys Ser Asp
        435                 440                 445
Gly Arg Thr Asp Tyr Val Lys Leu Phe Leu Pro Ile Ala Ile Arg Leu
    450                 455                 460
Arg Glu Asp Lys Thr Lys Ala Asn Thr Phe Glu Asp Val Phe Gly Asp
465                 470                 475                 480
Phe His Glu Val Thr Gly Leu Gly Ser Gly Ser Gly His His His
                485                 490                 495
His His His
```

<210> SEQ ID NO 9
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca agtttggcc aggtttaatt cctgaacaac tcaaatgct cgcaagttct      420 tatgatgaaa aaggcattaa taagaatatc aaatttccag cctttgctca gttaaaagct     480
gatggagctc ggtgttttgc tgaagttaga ggtgatgaat agatgatgt tcgtctttta     540 tcacgagctg gtaatgaata tctaggatta gatcttctta aggaagagtt aattaaaatg     600
accgctgaag cccgccagat tcatccagaa ggtgtgttga ttgatggcga attggtatac     660
catgagcaag ttaaaaagga gccagaaggc ctagattttc tttttgatgc ttatcctgaa     720
aacagtaaag ctaagaatt cgccgaagta gctgaatcac gtactgcttc taatggaatc     780
```

```
gccaataaat ctttaaaggg aaccatttct gaaaagaag cacaatgcat gaagtttcag    840
gtctgggatt atgtcccgtt ggtagaaata tacagtcttc ctgcatttcg tttgaaatat    900
gatgtacgtt tttctaaact agaacaaatg acatctggat atgataaagt aattttaatt    960
gaaaaccagg tagtaaataa cctagatgaa gctaaggtaa tttataaaaa gtatattgac   1020
caaggtcttg aaggtattat tctcaaaaat atcgatggat tatgggaaaa tgctcgttca   1080
aaaaatcttt ataaatttaa agaagtaatt aaagttgatt taaaaattgt aggaatttat   1140
cctcaccgta aagaccctac taaagcgggt ggatttattc ttgagtcaga gtgtggaaaa   1200
attaaggtaa atgctggttc aggcttaaaa gataaagccg gtgtaaaatc gcatgaactt   1260
gaccgtactc gcattatgga aaaccaaaat tattatattg gaaaaattct agagtgcgaa   1320
tgcaacggtt ggttaaaatc tgatggccgc actgattacg ttaaattatt tcttccgatt   1380
gcgattcgtt tacgtgaaga taaaactaaa gctaatacat tcgaagatgt atttggtgat   1440
tttcatgagg taactggtct aggttctggc agttcaggtc atcaccacca tcatcactaa   1500
```

<210> SEQ ID NO 10
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240
```

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Lys Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Gly His His
                485                 490                 495

His His His

<210> SEQ ID NO 11
<211> LENGTH: 1500
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 11
atgattctta aaattctgaa cgaaatagca tctattggtt caactaaaca gaagcaagca      60
attcttgaaa agaataaaga taatgaattg cttaaacgag tatatcgtct gactattct     120 cgtgggttac agtattatat caagaaatgg cctaaacctg tattgctac ccagagtttt     180 ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca agtttggcc aggtttaatt cctgaacaac tcaaatgct cgcaagttct     420 tatgatgaaa aaggcattaa taagaatatc aaatttccag cctttgctca gttaaaagct     480
gatggagctc ggtgttttgc tgaagttaga ggtgatgaat tagatgatgt tcgtcttta     540

-continued

```
tcacgagctg gtaatgaata tctaggatta gatcttctta aggaagagtt aattaaaatg    600
accgctgaag cccgccagat tcatccagaa ggtgtgttga ttgatggcga attggtatac    660
catgagcaag ttaaaaagga gccagaaggc ctagattttc tttttgatgc ttatcctgaa    720
aacagtaaag ctaaagaatt cgccgaagta gctgaatcac gtactgcttc taatggaatc    780
gccaataaat cttttaaggg aaccatttct gaaaagaag cacaatgcat gaagtttcag    840
gtctgggatt atgtcccgtt ggtagaaata tacagtcttc ctgcatttcg tttgaaatat    900
gatgtacgtt tttctaaact agaacaaatg acatctggat atgataaagt aattttaatt    960
gaaaaccagg tagtaaataa cctagatgaa gctaaggtaa tttataaaaa gtatattgac   1020
caaggtcttg aaggtattat tctcaaaaat atcgatggat tatgggaaaa tgctcgttca   1080
aaaaatcttt ataaatttaa agaagtaatt atggttgatt taaaaattgt aggaatttat   1140
cctcaccgta aagaccctac taaagcgggt ggatttattc ttgagtcaga gtgtggaaaa   1200
attaaggtaa atgctggttc aggcttaaaa gataaagccg gtgtaaaatc gcatgaactt   1260
gaccgtactc gcattatgga aaaccaaaat tattatattg gaaaaattct agagtgcgaa   1320
tgcaacggtt ggttaaaatc tgatggccgc actgattacg ttaaattatt tcttccgatt   1380
gcgattcgtt tacgtgaaga taaaactaaa gctaatacat cgaagatgt atttggtgat   1440
tttcatgagg taactggtct aggttctggc agttcaggtc atcaccacca tcatcactaa   1500
```

<210> SEQ ID NO 12
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

```
Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Met Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Gly His His
                485                 490                 495

His His His

<210> SEQ ID NO 13
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
```

```
ttgactggaa atgcagcaat tgaggaatta actggatata tcaccgatgg taaaaaagat    300
gatgttgaag ttttgcgtcg agtgatgatg cgagaccttg aatgtggtgc ttcagtatct    360
attgcaaaca aagtttggcc aggtttaatt cctgaacaac ctcaaatgct cgcaagttct    420
tatgatgaaa aaggcattaa taagaatatc aaatttccag cctttgctca gttaaaagct    480
gatggagctc ggtgttttgc tgaagttaga ggtgatgaat tagatgatgt tcgtctttta    540
tcacgagctg gtaatgaata tctaggatta gatcttctta aggaagagtt aattaaaatg    600
accgctgaag cccgccagat tcatccagaa ggtgtgttga ttgatggcga attggtatac    660
catgagcaag ttaaaaagga gccagaaggc ctagattttc tttttgatgc ttatcctgaa    720
aacagtaaag ctaaagaatt cgccgaagta gctgaatcac gtactgcttc taatggaatc    780
gccaataaat ctttaaaggg aaccatttct gaaaaagaag cacaatgcat gaagtttcag    840
gtctgggatt atgtcccgtt ggtagaaata tacagtcttc ctgcatttcg tttgaaatat    900
gatgtacgtt tttctaaact agaacaaatg acatctggat atgataaagt aattttaatt    960
gaaaaccagg tagtaaataa cctagatgaa gctaaggtaa tttataaaaa gtatattgac   1020
caaggtcttg aaggtattat tctcaaaaat atcgatggat tatgggaaaa tgctcgttca   1080
aaaaatcttt ataaatttaa agaagtaatt caagttgatt taaaaattgt aggaatttat   1140
cctcaccgta aagaccctac taaagcgggt ggatttattc ttgagtcaga gtgtggaaaa   1200
attaaggtaa atgctggttc aggcttaaaa gataaagccg tgtaaaatc gcatgaactt   1260 gaccgtactc gcattatgga aaaccaaaat tattatattg aaaaattct agagtgcgaa   1320 tgcaacggtt ggtaaaaatc tgatggccgc actgattacg ttaaattatt tcttccgatt   1380
gcgattcgtt tacgtgaaga taaaactaaa gctaatacat tcgaagatgt atttggtgat   1440
tttcatgagg taactggtct aggttctggc agttcaggtc atcaccacca tcatcactaa   1500
```

<210> SEQ ID NO 14
<211> LENGTH: 499
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 14

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
            165                 170                 175

Val Arg Leu Leu Ser Arg Ala Gly Asn Glu Tyr Leu Gly Leu Asp Leu
        180                 185                 190

Leu Lys Glu Glu Leu Ile Lys Met Thr Ala Glu Ala Arg Gln Ile His
    195                 200                 205

Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Gln Val Asp Leu Lys Ile Val Gly Ile Tyr Pro His Arg Lys
370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Ser Gly His His His
                485                 490                 495

His His His

<210> SEQ ID NO 15
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca agtttggcc aggtttaatt cctgaacaac ctcaaatgct cgcaagttct     420
tatgatgaaa aaggcattaa taagaatatc aaatttccag cctttgctca gttaaaagct     480
gatggagctc ggtgttttgc tgaagttaga ggtgatgaat tagatgatgt tcgtctttta     540
tcacgagctg gtaatgaata tctaggatta gatcttctta aggaagagtt aattaaaatg     600
accgctgaag cccgccagat tcatccagaa ggtgtgttga ttgatggcga attggtatac     660
catgagcaag ttaaaaagga gccagaaggc ctagattttc tttttgatgc ttatcctgaa     720
aacagtaaag ctaaagaatt cgccgaagta gctgaatcac gtactgcttc taatggaatc     780
gccaataaat ctttaaaggg aaccatttct gaaaagaag cacaatgcat gaagtttcag     840
gtctgggatt atgtcccgtt ggtagaaata tacagtcttc ctgcatttcg tttgaaatat     900
gatgtacgtt tttctaaact agaacaaatg acatctggat atgataaagt aattttaatt     960
gaaaaccagg tagtaaataa cctagatgaa gctaaggtaa tttataaaaa gtatattgac    1020
caaggtcttg aaggtattat tctcaaaaat atcgatggat atgggaaaa tgctcgttca    1080
aaaaatcttt ataaatttaa agaagtaatt cgtgttgatt taaaaattgt aggaatttat    1140
cctcaccgta aagaccctac taaagcgggt ggatttattc ttgagtcaga gtgtggaaaa    1200
attaaggtaa atgctggttc aggcttaaaa gataaagccg gtgtaaaatc gcatgaactt    1260
gaccgtactc gcattatgga aaaccaaaat tattatattg gaaaaattct agagtgcgaa    1320
tgcaacggtt ggttaaaatc tgatggccgc actgattacg ttaaattatt tcttccgatt    1380
gcgattcgtt tacgtgaaga taaaactaaa gctaatacat cgaagatgt atttggtgat    1440
tttcatgagg taactggtct aggttctggc agttcaggtc atcaccacca tcatcactaa    1500
```

<210> SEQ ID NO 16
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80
```

-continued

```
Leu Thr Gly Asn Ala Ala Ile Glu Glu Leu Thr Gly Tyr Ile Thr Asp
                    85                  90                  95
Gly Lys Lys Asp Asp Val Glu Val Leu Arg Arg Val Met Met Arg Asp
            100                 105                 110
Leu Glu Cys Gly Ala Ser Val Ser Ile Ala Asn Lys Val Trp Pro Gly
        115                 120                 125
Leu Ile Pro Glu Gln Pro Gln Met Leu Ala Ser Ser Tyr Asp Glu Lys
    130                 135                 140
Gly Ile Asn Lys Asn Ile Lys Phe Pro Ala Phe Ala Gln Leu Lys Ala
145                 150                 155                 160
Asp Gly Ala Arg Cys Phe Ala Glu Val Arg Gly Asp Glu Leu Asp Asp
                165                 170                 175
Val Arg Leu Leu Ser Arg Ala Gly Asn Glu Tyr Leu Gly Leu Asp Leu
            180                 185                 190
Leu Lys Glu Glu Leu Ile Lys Met Thr Ala Glu Ala Arg Gln Ile His
        195                 200                 205
Pro Glu Gly Val Leu Ile Asp Gly Glu Leu Val Tyr His Glu Gln Val
    210                 215                 220
Lys Lys Glu Pro Glu Gly Leu Asp Phe Leu Phe Asp Ala Tyr Pro Glu
225                 230                 235                 240
Asn Ser Lys Ala Lys Glu Phe Ala Glu Val Ala Glu Ser Arg Thr Ala
                245                 250                 255
Ser Asn Gly Ile Ala Asn Lys Ser Leu Lys Gly Thr Ile Ser Glu Lys
            260                 265                 270
Glu Ala Gln Cys Met Lys Phe Gln Val Trp Asp Tyr Val Pro Leu Val
        275                 280                 285
Glu Ile Tyr Ser Leu Pro Ala Phe Arg Leu Lys Tyr Asp Val Arg Phe
    290                 295                 300
Ser Lys Leu Glu Gln Met Thr Ser Gly Tyr Asp Lys Val Ile Leu Ile
305                 310                 315                 320
Glu Asn Gln Val Val Asn Asn Leu Asp Glu Ala Lys Val Ile Tyr Lys
                325                 330                 335
Lys Tyr Ile Asp Gln Gly Leu Glu Gly Ile Ile Leu Lys Asn Ile Asp
            340                 345                 350
Gly Leu Trp Glu Asn Ala Arg Ser Lys Asn Leu Tyr Lys Phe Lys Glu
        355                 360                 365
Val Ile Arg Val Asp Leu Lys Ile Val Gly Ile Tyr Pro His Arg Lys
    370                 375                 380
Asp Pro Thr Lys Ala Gly Gly Phe Ile Leu Glu Ser Glu Cys Gly Lys
385                 390                 395                 400
Ile Lys Val Asn Ala Gly Ser Gly Leu Lys Asp Lys Ala Gly Val Lys
                405                 410                 415
Ser His Glu Leu Asp Arg Thr Arg Ile Met Glu Asn Gln Asn Tyr Tyr
            420                 425                 430
Ile Gly Lys Ile Leu Glu Cys Glu Cys Asn Gly Trp Leu Lys Ser Asp
        435                 440                 445
Gly Arg Thr Asp Tyr Val Lys Leu Phe Leu Pro Ile Ala Ile Arg Leu
    450                 455                 460
Arg Glu Asp Lys Thr Lys Ala Asn Thr Phe Glu Asp Val Phe Gly Asp
465                 470                 475                 480
Phe His Glu Val Thr Gly Leu Gly Ser Gly Ser Ser Gly His His His
                485                 490                 495
His His His
```

<210> SEQ ID NO 17
<211> LENGTH: 1500
<212> TYPE: DNA
<213> ORGANISM: Artificial Sequence
<220> FEATURE:
<223> OTHER INFORMATION: Description of Artificial Sequence: Synthetic
        polynucleotide

<400> SEQUENCE: 17

```
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca aagtttggcc aggtttaatt cctgaacaac tcaaatgct cgcaagttct      420
tatgatgaaa aaggcattaa taagaatatc aaatttccag cctttgctca gttaaaagct     480
gatggagctc ggtgttttgc tgaagttaga ggtgatgaat tagatgatgt tcgtcttta     540
tcacgagctg gtaatgaata tctaggatta gatcttctta aggaagagtt aattaaaatg    600
accgctgaag cccgccagat tcatccagaa ggtgtgttga ttgatggcga attggtatac    660
catgagcaag ttaaaaagga gccagaaggc ctagattttc tttttgatgc ttatcctgaa    720
aacagtaaag ctaagaatt cgccgaagta gctgaatcac gtactgcttc taatggaatc    780
gccaataaat ctttaaaggg aaccatttct gaaaagaag cacaatgcat gaagtttcag    840
gtctgggatt atgtcccgtt ggtagaaata tacagtcttc ctgcatttcg tttgaaatat    900
gatgtacgtt tttctaaact agaacaaatg acatctggat atgataaagt aatttaatt     960
gaaaaccagg tagtaaataa cctagatgaa gctaaggtaa tttataaaaa gtatattgac   1020
caaggtcttg aaggtattat tctcaaaaat atcgatggat tatgggaaaa tgctcgttca   1080
aaaaatcttt ataaatttaa agaagtaatt actgttgatt taaaattgt aggaatttat    1140
cctcaccgta agaccctac taaagcgggt ggatttattc ttgagtcaga gtgtggaaaa   1200
attaaggtaa atgctggttc aggcttaaaa gataaagccg gtgtaaaatc gcatgaactt   1260
gaccgtactc gcattatgga aaaccaaaat tattatattg gaaaaattct agagtgcgaa   1320
tgcaacggtt ggttaaaatc tgatggccgc actgattacg ttaaattatt tcttccgatt   1380
gcgattcgtt tacgtgaaga taaaactaaa gctaatacat tcgaagatgt atttggtgat   1440
tttcatgagg taactggtct aggttctggc agttcaggtc atcaccacca tcatcactaa   1500
```

<210> SEQ ID NO 18
<211> LENGTH: 499
<212> TYPE: PRT
<213> ORGANISM: Artificial Sequence
<220> FEATURE:
<223> OTHER INFORMATION: Description of Artificial Sequence: Synthetic
        polypeptide

<400> SEQUENCE: 18

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

-continued

```
Arg Val Tyr Arg Leu Thr Tyr Ser Arg Gly Leu Gln Tyr Ile Lys
             35                  40                  45
Lys Trp Pro Lys Pro Gly Ile Ala Thr Gln Ser Phe Gly Met Leu Thr
 50                  55                  60
Leu Thr Asp Met Leu Asp Phe Ile Glu Phe Thr Leu Ala Thr Arg Lys
 65                  70                  75                  80
Leu Thr Gly Asn Ala Ala Ile Glu Glu Leu Thr Gly Tyr Ile Thr Asp
                 85                  90                  95
Gly Lys Lys Asp Asp Val Glu Val Leu Arg Arg Val Met Met Arg Asp
                100                 105                 110
Leu Glu Cys Gly Ala Ser Val Ser Ile Ala Asn Lys Val Trp Pro Gly
                115                 120                 125
Leu Ile Pro Glu Gln Pro Gln Met Leu Ala Ser Ser Tyr Asp Glu Lys
                130                 135                 140
Gly Ile Asn Lys Asn Ile Lys Phe Pro Ala Phe Ala Gln Leu Lys Ala
145                 150                 155                 160
Asp Gly Ala Arg Cys Phe Ala Glu Val Arg Gly Asp Glu Leu Asp Asp
                165                 170                 175
Val Arg Leu Leu Ser Arg Ala Gly Asn Glu Tyr Leu Gly Leu Asp Leu
                180                 185                 190
Leu Lys Glu Glu Leu Ile Lys Met Thr Ala Glu Ala Arg Gln Ile His
                195                 200                 205
Pro Glu Gly Val Leu Ile Asp Gly Glu Leu Val Tyr His Glu Gln Val
                210                 215                 220
Lys Lys Glu Pro Glu Gly Leu Asp Phe Leu Phe Asp Ala Tyr Pro Glu
225                 230                 235                 240
Asn Ser Lys Ala Lys Glu Phe Ala Glu Val Ala Glu Ser Arg Thr Ala
                245                 250                 255
Ser Asn Gly Ile Ala Asn Lys Ser Leu Lys Gly Thr Ile Ser Glu Lys
                260                 265                 270
Glu Ala Gln Cys Met Lys Phe Gln Val Trp Asp Tyr Val Pro Leu Val
                275                 280                 285
Glu Ile Tyr Ser Leu Pro Ala Phe Arg Leu Lys Tyr Asp Val Arg Phe
                290                 295                 300
Ser Lys Leu Glu Gln Met Thr Ser Gly Tyr Asp Lys Val Ile Leu Ile
305                 310                 315                 320
Glu Asn Gln Val Val Asn Asn Leu Asp Glu Ala Lys Val Ile Tyr Lys
                325                 330                 335
Lys Tyr Ile Asp Gln Gly Leu Glu Gly Ile Ile Leu Lys Asn Ile Asp
                340                 345                 350
Gly Leu Trp Glu Asn Ala Arg Ser Lys Asn Leu Tyr Lys Phe Lys Glu
                355                 360                 365
Val Ile Thr Val Asp Leu Lys Ile Val Gly Ile Tyr Pro His Arg Lys
                370                 375                 380
Asp Pro Thr Lys Ala Gly Gly Phe Ile Leu Glu Ser Glu Cys Gly Lys
385                 390                 395                 400
Ile Lys Val Asn Ala Gly Ser Gly Leu Lys Asp Lys Ala Gly Val Lys
                405                 410                 415
Ser His Glu Leu Asp Arg Thr Arg Ile Met Glu Asn Gln Asn Tyr Tyr
                420                 425                 430
Ile Gly Lys Ile Leu Glu Cys Glu Cys Asn Gly Trp Leu Lys Ser Asp
                435                 440                 445
```

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Ser Gly His His His
                485                 490                 495

His His His

<210> SEQ ID NO 19
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca agtttggcc aggtttaatt cctgaacaac ctcaaatgct cgcaagttct     420
tatgatgaaa aaggcattaa taagaatatc aaatttccag cctttgctca gttaaaagct     480
gatggagctc ggtgttttgc tgaagttaga ggtgatgaat tagatgatgt tcgtctttta     540
tcacgagctg gtaatgaata tctaggatta gatcttctta aggaagagtt aattaaaatg     600
accgctgaag cccgccagat tcatccagaa ggtgtgttga ttgatggcga attggtatac     660
catgagcaag ttaaaaagga gccagaaggc ctagattttc tttttgatgc ttatcctgaa     720
aacagtaaag ctaagaatt cgccgaagta gctgaatcac gtactgcttc taatggaatc     780
gccaataaat ctttaaaggg aaccattcct gaaaaagaag cacaatgcat gaagtttcag     840
gtctgggatt atgtcccgtt ggtagaaata tacagtcttc ctgcatttcg tttgaaatat     900
gatgtacgtt tttctaaact agaacaaatg acatctggat atgataaagt aattttaatt     960
gaaaaccagg tagtaaataa cctagatgaa gctaaggtaa tttataaaaa gtatattgac    1020
caaggtcttg aaggtattat tctcaaaaat atcgatggat tatgggaaaa tgctcgttca    1080
aaaaatcttt ataaatttaa agaagtaatt gttgttgatt taaaaattgt aggaatttat    1140
cctcaccgta aagaccctac taaagcgggt ggatttattc ttgagtcaga gtgtggaaaa    1200
attaaggtaa atgctggttc aggcttaaaa gataaagccg gtgtaaaatc gcatgaactt    1260
gaccgtactc gcattatgga aaccaaaat tattatattg gaaaaattct agagtgcgaa    1320
tgcaacggtt ggttaaaatc tgatggccgc actgattacg ttaaattatt tcttccgatt    1380
gcgattcgtt tacgtgaaga taaaactaaa gctaatacat cgaagatgt atttggtgat    1440 tttcatgagg taactggtct aggttctggc agttcaggtc atcaccacca tcatcactaa    1500

<210> SEQ ID NO 20
<211> LENGTH: 499
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 20

```
Met Ile Leu Lys Ile Leu Asn Glu Ile Ala Ser Ile Gly Ser Thr Lys
1               5                   10                  15

Gln Lys Gln Ala Ile Leu Glu Lys Lys Asn Asp Glu Leu Leu Lys
            20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
        50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Val Val Asp Leu Lys Ile Val Gly Ile Tyr Pro His Arg Lys
370                 375                 380

Asp Pro Thr Lys Ala Gly Gly Phe Ile Leu Glu Ser Glu Cys Gly Lys
385                 390                 395                 400
```

```
Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
                435                 440                 445

Gly Arg Thr Asp Tyr Val Lys Leu Phe Leu Pro Ile Ala Ile Arg Leu
        450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Ser Gly His His His
                485                 490                 495

His His His

<210> SEQ ID NO 21
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
atgattctta aaattctgaa cgaaatagca tctattggtt caactaaaca gaagcaagca        60
attcttgaaa agaataaaga taatgaattg cttaaacgag tatatcgtct gacttattct       120
cgtgggttac agtattatat caagaaatgg cctaaacctg gtattgctac ccagagtttt       180
ggaatgttga ctcttaccga tatgcttgac ttcattgaat tcacattagc tactcggaaa       240
ttgactggaa atgcagcaat tgaggaatta actggatata tcaccgatgg taaaaaagat       300
gatgttgaag ttttgcgtcg agtgatgatg cgagaccttg aatgtggtgc ttcagtatct       360
attgcaaaca agtttggcc aggtttaatt cctgaacaac tcaaatgct cgcaagttct         420 tatgatgaaa aaggcattaa taagaatatc aaatttccag cctttgctca gttaaaagct       480
gatggagctc ggtgttttgc tgaagttaga ggtgatgaat tagatgatgt tcgtctttta       540
tcacgagctg gtaatgaata tctaggatta gatcttctta aggaagagtt aattaaaatg       600
accgctgaag cccgccagat tcatccagaa ggtgtgttga ttgatggcga attggtatac       660
catgagcaag ttaaaaagga gccagaaggc ctagattttc ttttttgatgc ttatcctgaa      720 aacagtaaag ctaagaatt cgccgaagta gctgaatcac gtactgcttc taatggaatc       780
gccaataaat ctttaaaggg aaccatttct gaaaagaag cacaatgcat gaagtttcag        840
gtctgggatt atgtcccgtt ggtagaaata tacagtcttc ctgcatttcg tttgaaatat       900
gatgtacgtt tttctaaact agaacaaatg acatctggat atgataaagt aattttaatt      960
gaaaaccagg tagtaaataa cctagatgaa gctaaggtaa tttataaaaa gtatattgac     1020
caaggtcttg aaggtattat tctcaaaaat atcgatggat tatgggaaaa tgctcgttca     1080
aaaaatcttt ataaatttaa agaagtaatt tacgttgatt taaaaattgt aggaatttat     1140
cctcaccgta agaccctac taaagcgggt ggatttattc ttgagtcaga gtgtggaaaa      1200
attaaggtaa atgctggttc aggcttaaaa gataaagccg gtgtaaaatc gcatgaactt     1260
gaccgtactc gcattatgga aaaccaaaat tattatattg gaaaaattct agagtgcgaa     1320
tgcaacggtt ggttaaaatc tgatggccgc actgattacg ttaaattatt tcttccgatt     1380
```
gcgattcgtt tacgtgaaga taaaactaaa gctaatacat tcgaagatgt atttggtgat    1440
tttcatgagg taactggtct aggttctggc agttcaggtc atcaccacca tcatcactaa    1500

<210> SEQ ID NO 22
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

```
Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Glu
            355                 360                 365

Val Ile Tyr Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Ser Gly His His His
                485                 490                 495

His His His
```

<210> SEQ ID NO 23
<211> LENGTH: 1500
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

```
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca agtttggcc aggtttaatt cctgaacaac ctcaaatgct cgcaagttct     420
tatgatgaaa aaggcattaa taagaatatc aaatttccag cctttgctca gttaaaagct     480
gatggagctc ggtgttttgc tgaagttaga ggtgatgaat agatgatgt tcgtctttta     540
tcacgagctg gtaatgaata tctaggatta gatcttctta aggaagagtt aattaaaatg     600
accgctgaag cccgccagat tcatccagaa ggtgtgttga ttgatggcga attggtatac     660
catgagcaag ttaaaaagga gccagaaggc ctagattttc tttttgatgc ttatcctgaa     720
aacagtaaag ctaaagaatt cgccgaagta gctgaatcac gtactgcttc taatggaatc     780
gccaataaat ctttaaaggg aaccatttct gaaaagaag cacaatgcat gaagtttcag     840
gtctgggatt atgtcccgtt ggtagaaata tacagtcttc ctgcatttcg tttgaaatat     900
gatgtacgtt tttctaaact agaacaaatg acatctggat atgataaagt aatttttaatt     960
gaaaccagg tagtaaataa cctagatgaa gctaaggtaa tttataaaaa gtatattgac    1020
caaggtcttg aaggtattat tctcaaaaat atcgatggat tatgggaaaa tgctcgttca    1080
```

```
aaaaatctttt ataaatttaa agaagtaatt gatgttgatt taaaaattgt aggaatttat    1140
cctcaccgta aagaccctac taaagcgggt ggatttattc ttgagtcaga gtgtggaaaa    1200
attaaggtaa atgctggttc aggcttaaaa gataaagccg gtgtaaaatc gcatgaactt    1260
gaccgtactc gcattatgga aaaccaaaat tattatattg gaaaaattct aaaatgcgaa    1320
tgcaacggtt ggttaaaatc tgatggccgc actgattacg ttaaattatt tcttccgatt    1380
gcgattcgtt tacgtgaaga taaaactaaa gctaatacat tcgaagatgt atttggtgat    1440
tttcatgagg taactggtct aggttctggc agttcaggtc atcaccacca tcatcactaa    1500
```

<210> SEQ ID NO 24
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285
```

```
Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Glu
    355                 360                 365

Val Ile Asp Val Asp Leu Lys Ile Val Gly Ile Tyr Pro His Arg Lys
370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Lys Cys Glu Cys Asn Gly Trp Leu Lys Ser Asp
    435                 440                 445

Gly Arg Thr Asp Tyr Val Lys Leu Phe Leu Pro Ile Ala Ile Arg Leu
450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Ser Gly His His His
                485                 490                 495

His His His

<210> SEQ ID NO 25
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca agtttggcc aggtttaatt cctgaacaac ctcaaatgct cgcaagttct     420
tatgatgaaa aaggcattaa taagaatatc aaatttccag cctttgctca gttaaaagct     480
gatggagctc ggtgttttgc tgaagttaga ggtgatgaat agatgatgt cgtctttta     540 tcacgagctg gtaatgaata tctaggatta gatcttctta aggaagagtt aattaaaatg     600
accgctgaag cccgccagat tcatccagaa ggtgtgttga ttgatggcga attggtatac     660
catgagcaag ttaaaaagga gccagaaggc ctagattttc ttttgatgc ttatcctgaa     720 aacagtaaag ctaagaatt cgccgaagta gctgaatcac gtactgcttc taatggaatc     780
gccaataaat cttttaaggg aaccattct gaaaagaag cacaatgcat gaagtttcag     840
```

-continued

```
gtctgggatt atgtcccgtt ggtagaaata tacagtcttc ctgcatttcg tttgaaatat    900
gatgtacgtt tttctaaact agaacaaatg acatctggat atgataaagt aattttaatt    960
gaaaaccagg tagtaaataa cctagatgaa gctaaggtaa tttataaaaa gtatattgac   1020
caaggtcttg aaggtattat tctcaaaaat atcgatggat tatgggaaaa tgctcgttca   1080
aaaaatcttt ataaatttaa agaagtaatt gatgttgatt taaaaattgt aggaatttat   1140
cctcaccgta aagaccctac taaagcgggt ggatttattc ttgagtcaga gtgtggaaaa   1200
attaaggtaa atgctggttc aggcttaaaa gataaagccg gtgtaaaatc gcatgaactt   1260
gaccgtactc gcattatgga aaaccaaaat tattatattg aaaaattct agagtgcaaa    1320 tgcaacggtt ggttaaaatc tgatggccgc actgattacg ttaaattatt tcttccgatt   1380
gcgattcgtt tacgtgaaga taaaactaaa gctaatacat tcgaagatgt atttggtgat   1440
tttcatgagg taactggtct aggttctggc agttcaggtc atcaccacca tcatcactaa   1500
```

<210> SEQ ID NO 26
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
             245                 250                 255
Ser Asn Gly Ile Ala Asn Lys Ser Leu Lys Gly Thr Ile Ser Glu Lys
        260                 265                 270
Glu Ala Gln Cys Met Lys Phe Gln Val Trp Asp Tyr Val Pro Leu Val
    275                 280                 285
Glu Ile Tyr Ser Leu Pro Ala Phe Arg Leu Lys Tyr Asp Val Arg Phe
290                 295                 300
Ser Lys Leu Glu Gln Met Thr Ser Gly Tyr Asp Lys Val Ile Leu Ile
305                 310                 315                 320
Glu Asn Gln Val Val Asn Asn Leu Asp Glu Ala Lys Val Ile Tyr Lys
                325                 330                 335
Lys Tyr Ile Asp Gln Gly Leu Glu Gly Ile Ile Leu Lys Asn Ile Asp
            340                 345                 350
Gly Leu Trp Glu Asn Ala Arg Ser Lys Asn Leu Tyr Lys Phe Lys Glu
        355                 360                 365
Val Ile Asp Val Asp Leu Lys Ile Val Gly Ile Tyr Pro His Arg Lys
    370                 375                 380
Asp Pro Thr Lys Ala Gly Gly Phe Ile Leu Glu Ser Glu Cys Gly Lys
385                 390                 395                 400
Ile Lys Val Asn Ala Gly Ser Gly Leu Lys Asp Lys Ala Gly Val Lys
                405                 410                 415
Ser His Glu Leu Asp Arg Thr Arg Ile Met Glu Asn Gln Asn Tyr Tyr
            420                 425                 430
Ile Gly Lys Ile Leu Glu Cys Lys Cys Asn Gly Trp Leu Lys Ser Asp
        435                 440                 445
Gly Arg Thr Asp Tyr Val Lys Leu Phe Leu Pro Ile Ala Ile Arg Leu
    450                 455                 460
Arg Glu Asp Lys Thr Lys Ala Asn Thr Phe Glu Asp Val Phe Gly Asp
465                 470                 475                 480
Phe His Glu Val Thr Gly Leu Gly Ser Gly Ser Ser Gly His His His
                485                 490                 495
His His His

<210> SEQ ID NO 27
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
atgattctta aaattctgaa cgaaatagca tctattggtt caactaaaca gaagcaagca    60
attcttgaaa agaataaaga taatgaattg cttaaacgag tatatcgtct gacttattct   120
cgtgggttac agtattatat caagaaatgg cctaaacctg gtattgctac ccagagtttt   180
ggaatgttga ctcttaccga tatgcttgac ttcattgaat tcacattagc tactcggaaa   240
ttgactggaa atgcagcaat tgaggaatta actggatata tcaccgatgg taaaaaagat   300
gatgttgaag ttttgcgtcg agtgatgatg cgagaccttg aatgtggtgc ttcagtatct   360
attgcaaaca agtttggccc aggtttaatt cctgaacaac tcaaatgctc cgcaagttct   420
tatgatgaaa aaggcattaa taagaatatc aaatttccag cctttgctca gttaaaagct   480
gatggagctc ggtgttttgc tgaagttaga ggtgatgaat tagatgatgt tcgtctttta   540

```
tcacgagctg gtaatgaata tctaggatta gatcttctta aggaagagtt aattaaaatg    600
accgctgaag cccgccagat tcatccagaa ggtgtgttga ttgatggcga attggtatac    660
catgagcaag ttaaaaagga gccagaaggc ctagattttc tttttgatgc ttatcctgaa    720
aacagtaaag ctaaagaatt cgccgaagta gctgaatcac gtactgcttc taatggaatc    780
gccaataaat cttaaaggg aaccatttct gaaaagaag cacaatgcat gaagtttcag    840
gtctgggatt atgtcccgtt ggtagaaata tacagtcttc ctgcatttcg tttgaaatat    900
gatgtacgtt tttctaaact agaacaaatg acatctggat atgataaagt aattttaatt    960
gaaaaccagg tagtaaataa cctagatgaa gctaaggtaa tttataaaaa gtatattgac   1020
caaggtcttg aaggtattat tctcaaaaat atcgatggat tatgggaaaa tgctcgttca   1080
aaaaatcttt ataaatttaa agaagtaatt gatgttgatt taaaaattgt aggaatttat   1140
cctcaccgta aagaccctac taaagcgggt ggatttattc ttgagtcaga gtgtggaaaa   1200
attaaggtaa atgctggttc aggcttaaaa gataaagccg gtgtaaaatc gcatgaactt   1260
gaccgtactc gcattatgga aaaccaaaat tattatattg gaaaaattct agagtgccgt   1320
tgcaacggtt ggttaaaatc tgatggccgc actgattacg ttaaattatt tcttccgatt   1380
gcgattcgtt tacgtgaaga taaaactaaa gctaatacat cgaagatgt atttggtgat   1440 tttcatgagg taactggtct aggttctggc agttcaggtc atcaccacca tcatcactaa   1500
```

```
<210> SEQ ID NO 28
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190
```

Leu Lys Glu Glu Leu Ile Lys Met Thr Ala Glu Ala Arg Gln Ile His
                195                 200                 205

Pro Glu Gly Val Leu Ile Asp Gly Glu Leu Val Tyr His Glu Gln Val
        210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
                260                 265                 270

Glu Ala Gln Cys Met Lys Phe Gln Val Trp Asp Tyr Val Pro Leu Val
                275                 280                 285

Glu Ile Tyr Ser Leu Pro Ala Phe Arg Leu Lys Tyr Asp Val Arg Phe
                290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Glu
                355                 360                 365

Val Ile Asp Val Asp Leu Lys Ile Val Gly Ile Tyr Pro His Arg Lys
                370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Glu Cys Arg Cys Asn Gly Trp Leu Lys Ser Asp
                435                 440                 445

Gly Arg Thr Asp Tyr Val Lys Leu Phe Leu Pro Ile Ala Ile Arg Leu
450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Gly His His His
                485                 490                 495

His His His

<210> SEQ ID NO 29
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
atgattctta aaattctgaa cgaaatagca tctattggtt caactaaaca gaagcaagca        60
attcttgaaa agaataaaga taatgaattg cttaaacgag tatatcgtct gacttattct       120
cgtgggttac agtattatat caagaaatgg cctaaacctg gtattgctac ccagagtttt       180
ggaatgttga ctcttaccga tatgcttgac ttcattgaat tcacattagc tactcggaaa       240
ttgactggaa atgcagcaat tgaggaatta actggatata tcaccgatgg taaaaaagat       300

```
gatgttgaag ttttgcgtcg agtgatgatg cgagaccttg aatgtggtgc ttcagtatct    360
attgcaaaca aagtttggcc aggtttaatt cctgaacaac ctcaaatgct cgcaagttct    420
tatgatgaaa aaggcattaa taagaatatc aaatttccag cctttgctca gttaaaagct    480
gatggagctc ggtgttttgc tgaagttaga ggtgatgaat tagatgatgt tcgtcttta    540 tcacgagctg gtaatgaata tctaggatta gatcttctta aggaagagtt aattaaaatg    600
accgctgaag cccgccagat tcatccagaa ggtgtgttga ttgatggcga attggtatac    660
catgagcaag ttaaaaagga gccagaaggc ctagattttc ttttgatgc ttatcctgaa     720 aacagtaaag ctaaagaatt cgccgaagta gctgaatcac gtactgcttc taatggaatc    780
gccaataaat cttaaaggg aaccatttct gaaaagaag cacaatgcat gaagtttcag      840
gtctgggatt atgtccgtt ggtagaaata tacagtcttc ctgcatttcg tttgaaatat     900
gatgtacgtt tttctaaact agaacaaatg acatctggat atgataaagt aatttaatt   960 gaaaaccagg tagtaaataa cctagatgaa gctaaggtaa tttataaaaa gtatattgac  1020
caaggtcttg aaggtattat tctcaaaaat atcgatggat tatgggaaaa tgctcgttca  1080
aaaaatcttt ataaatttaa agaagtaatt gatgttgatt taaaaattgt aggaatttat  1140
cctcaccgta agaccctac taaagcgggt ggatttattc ttgagtcaga gtgtggaaaa   1200
attaaggtaa atgctggttc aggcttaaaa gataaagccg gtgtaaaatc gcatgaactt  1260
gaccgtactc gcattatgga aaaccaaaat tattatattg gaaaaattct agagtgctct  1320
tgcaacggtt ggttaaaatc tgatggccgc actgattacg ttaaattatt tcttccgatt  1380
gcgattcgtt tacgtgaaga taaaactaaa gctaatacat tcgaagatgt atttggtgat  1440
tttcatgagg taactggtct aggttctggc agttcaggtc atcaccacca tcatcactaa  1500
```

<210> SEQ ID NO 30
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140
```

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
            165                 170                 175

Val Arg Leu Leu Ser Arg Ala Gly Asn Glu Tyr Leu Gly Leu Asp Leu
        180                 185                 190

Leu Lys Glu Glu Leu Ile Lys Met Thr Ala Glu Ala Arg Gln Ile His
    195                 200                 205

Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
            245                 250                 255

Ser Asn Gly Ile Ala Asn Lys Ser Leu Lys Gly Thr Ile Ser Glu Lys
        260                 265                 270

Glu Ala Gln Cys Met Lys Phe Gln Val Trp Asp Tyr Val Pro Leu Val
    275                 280                 285

Glu Ile Tyr Ser Leu Pro Ala Phe Arg Leu Lys Tyr Asp Val Arg Phe
290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
            325                 330                 335

Lys Tyr Ile Asp Gln Gly Leu Glu Gly Ile Ile Leu Lys Asn Ile Asp
        340                 345                 350

Gly Leu Trp Glu Asn Ala Arg Ser Lys Asn Leu Tyr Lys Phe Lys Glu
    355                 360                 365

Val Ile Asp Val Asp Leu Lys Ile Val Gly Ile Tyr Pro His Arg Lys
370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
            405                 410                 415

Ser His Glu Leu Asp Arg Thr Arg Ile Met Glu Asn Gln Asn Tyr Tyr
        420                 425                 430

Ile Gly Lys Ile Leu Glu Cys Ser Cys Asn Gly Trp Leu Lys Ser Asp
    435                 440                 445

Gly Arg Thr Asp Tyr Val Lys Leu Phe Leu Pro Ile Ala Ile Arg Leu
450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Ser Gly His His His
            485                 490                 495

His His His

<210> SEQ ID NO 31
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
atgattctta aaattctgaa cgaaatagca tctattggtt caactaaaca gaagcaagca        60
attcttgaaa agaataaaga taatgaattg cttaaacgag tatatcgtct gacttattct       120
cgtgggttac agtattatat caagaaatgg cctaaacctg gtattgctac ccagagtttt       180
ggaatgttga ctcttaccga tatgcttgac ttcattgaat tcacattagc tactcggaaa       240
ttgactggaa atgcagcaat tgaggaatta actggatata tcaccgatgg taaaaaagat       300
gatgttgaag ttttgcgtcg agtgatgatg cgagaccttg aatgtggtgc ttcagtatct       360
attgcaaaca agtttggcc aggtttaatt cctgaacaac ctcaaatgct cgcaagttct       420
tatgatgaaa aaggcattaa taagaatatc aaatttccag cctttgctca gttaaaagct       480
gatggagctc ggtgttttgc tgaagttaga ggtgatgaat tagatgatgt tcgtctttta       540
tcacgagctg gtaatgaata tctaggatta gatcttctta aggaagagtt aattaaaatg       600
accgctgaag cccgccagat tcatccagaa ggtgtgttga ttgatggcga attggtatac       660
catgagcaag ttaaaaagga gccagaaggc ctagattttc ttttttgatgc ttatcctgaa       720
aacagtaaag ctaaagaatt cgccgaagta gctgaatcac gtactgcttc taatggaatc       780
gccaataaat ctttaaaggg aaccatttct gaaaaagaag cacaatgcat gaagtttcag       840
gtctgggatt atgtcccgtt ggtagaaata tacagtcttc ctgcatttcg tttgaaatat       900
gatgtacgtt tttctaaact agaacaaatg acatctggat atgataaagt aattttaatt       960
gaaaaccagg tagtaaataa cctagatgaa gctaaggtaa tttataaaaa gtatattgac      1020
caaggtcttg aaggtattat tctcaaaaat atcgatggat atgggaaaa tgctcgttca       1080
aaaaatcttt ataaatttaa agaagtaatt gatgttgatt taaaaattgt aggaatttat      1140
cctcaccgta aagaccctac taaagcgggt ggatttattc ttgagtcaga gtgtggaaaa      1200
attaaggtaa atgctggttc aggcttaaaa gataaagccg gtgtaaaatc gcatgaactt      1260
gaccgtactc gcattatgga aaaccaaaat tattatattg gaaaaattct agagtgcgaa      1320
tgcaacggtt ggttaaaatc tgatggccgc actgattacg ttaaattatt tcttccgatt      1380
gcgattcgtt tacgtaaaga taaaactaaa gctaatacat tcgaagatgt atttggtgat      1440
tttcatgagg taactggtct aggttctggc agttcaggtc atcaccacca tcatcactaa      1500
```

<210> SEQ ID NO 32
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

```
Leu Thr Gly Asn Ala Ala Ile Glu Glu Leu Thr Gly Tyr Ile Thr Asp
                85                  90                  95
Gly Lys Lys Asp Asp Val Glu Val Leu Arg Arg Val Met Met Arg Asp
            100                 105                 110
Leu Glu Cys Gly Ala Ser Val Ser Ile Ala Asn Lys Val Trp Pro Gly
            115                 120                 125
Leu Ile Pro Glu Gln Pro Gln Met Leu Ala Ser Ser Tyr Asp Glu Lys
            130                 135                 140
Gly Ile Asn Lys Asn Ile Lys Phe Pro Ala Phe Ala Gln Leu Lys Ala
145                 150                 155                 160
Asp Gly Ala Arg Cys Phe Ala Glu Val Arg Gly Asp Glu Leu Asp Asp
                165                 170                 175
Val Arg Leu Leu Ser Arg Ala Gly Asn Glu Tyr Leu Gly Leu Asp Leu
            180                 185                 190
Leu Lys Glu Glu Leu Ile Lys Met Thr Ala Glu Ala Arg Gln Ile His
            195                 200                 205
Pro Glu Gly Val Leu Ile Asp Gly Glu Leu Val Tyr His Glu Gln Val
    210                 215                 220
Lys Lys Glu Pro Glu Gly Leu Asp Phe Leu Phe Asp Ala Tyr Pro Glu
225                 230                 235                 240
Asn Ser Lys Ala Lys Glu Phe Ala Glu Val Ala Glu Ser Arg Thr Ala
                245                 250                 255
Ser Asn Gly Ile Ala Asn Lys Ser Leu Lys Gly Thr Ile Ser Glu Lys
            260                 265                 270
Glu Ala Gln Cys Met Lys Phe Gln Val Trp Asp Tyr Val Pro Leu Val
            275                 280                 285
Glu Ile Tyr Ser Leu Pro Ala Phe Arg Leu Lys Tyr Asp Val Arg Phe
    290                 295                 300
Ser Lys Leu Glu Gln Met Thr Ser Gly Tyr Asp Lys Val Ile Leu Ile
305                 310                 315                 320
Glu Asn Gln Val Val Asn Asn Leu Asp Glu Ala Lys Val Ile Tyr Lys
                325                 330                 335
Lys Tyr Ile Asp Gln Gly Leu Glu Gly Ile Ile Leu Lys Asn Ile Asp
            340                 345                 350
Gly Leu Trp Glu Asn Ala Arg Ser Lys Asn Leu Tyr Lys Phe Lys Glu
            355                 360                 365
Val Ile Asp Val Asp Leu Lys Ile Val Gly Ile Tyr Pro His Arg Lys
    370                 375                 380
Asp Pro Thr Lys Ala Gly Gly Phe Ile Leu Glu Ser Glu Cys Gly Lys
385                 390                 395                 400
Ile Lys Val Asn Ala Gly Ser Gly Leu Lys Asp Lys Ala Gly Val Lys
                405                 410                 415
Ser His Glu Leu Asp Arg Thr Arg Ile Met Glu Asn Gln Asn Tyr Tyr
            420                 425                 430
Ile Gly Lys Ile Leu Glu Cys Glu Cys Asn Gly Trp Leu Lys Ser Asp
            435                 440                 445
Gly Arg Thr Asp Tyr Val Lys Leu Phe Leu Pro Ile Ala Ile Arg Leu
    450                 455                 460
Arg Lys Asp Lys Thr Lys Ala Asn Thr Phe Glu Asp Val Phe Gly Asp
465                 470                 475                 480
Phe His Glu Val Thr Gly Leu Gly Ser Gly Ser Ser Gly His His His
                485                 490                 495
His His His
```

<210> SEQ ID NO 33
<211> LENGTH: 1500
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33

```
atgattctta aaattctgaa cgaaatagca tctattggtt caactaaaca gaagcaagca     60
attcttgaaa agaataaaga taatgaattg cttaaacgag tatatcgtct gacttattct    120
cgtgggttac agtattatat caagaaatgg cctaaacctg gtattgctac ccagagtttt    180
ggaatgttga ctcttaccga tatgcttgac ttcattgaat tcacattagc tactcggaaa    240
ttgactggaa atgcagcaat tgaggaatta actggatata tcaccgatgg taaaaaagat    300
gatgttgaag ttttgcgtcg agtgatgatg cgagaccttg aatgtggtgc ttcagtatct    360
attgcaaaca aagtttggcc aggtttaatt cctgaacaac tcaaatgct cgcaagttct     420
tatgatgaaa aaggcattaa taagaatatc aaatttccag cctttgctca gttaaaagct    480
gatggagctc ggtgttttgc tgaagttaga ggtgatgaat tagatgatgt tcgtcttta     540
tcacgagctg gtaatgaata tctaggatta gatcttctta aggaagagtt aattaaaatg    600
accgctgaag cccgccagat tcatccagaa ggtgtgttga ttgatggcga attggtatac    660
catgagcaag ttaaaaagga gccagaaggc ctagattttc tttttgatgc ttatcctgaa    720
aacagtaaag ctaagaatt cgccgaagta gctgaatcac gtactgcttc taatggaatc     780
gccaataaat ctttaaaggg aaccatttct gaaaagaag cacaatgcat gaagtttcag     840
gtctgggatt atgtcccgtt ggtagaaata tacagtcttc ctgcatttcg tttgaaatat    900
gatgtacgtt tttctaaact agaacaaatg acatctggat atgataaagt aatttaatt    960
gaaaaccagg tagtaaataa cctagatgaa gctaaggtaa tttataaaaa gtatattgac   1020
caaggtcttg aaggtattat tctcaaaaat atcgatggat tatgggaaaa tgctcgttca   1080
aaaatctttt ataaatttaa agaagtaatt gatgttgatt taaaaattgt aggaatttat   1140
cctcaccgta aagaccctac taaagcgggt ggatttattc ttgagtcaga gtgtggaaaa   1200
attaaggtaa atgctggttc aggcttaaaa gataaagccg gtgtaaaatc gcatgaactt   1260
gaccgtactc gcattatgga aaaccaaaat tattatattg gaaaaattct agagtgcgaa   1320
tgcaacggtt ggttaaaatc tgatggccgc actgattacg ttaaattatt tcttccgatt   1380
gcgattcgtt tacgtgaaga taaaactaaa gctaatacat cgaagatgt atttggtgat    1440
tttcataaag taactggtct aggttctggc agttcaggtc atcaccacca tcatcactaa   1500
```

<210> SEQ ID NO 34
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

```
Arg Val Tyr Arg Leu Thr Tyr Ser Arg Gly Leu Gln Tyr Ile Lys
            35                  40                  45

Lys Trp Pro Lys Pro Gly Ile Ala Thr Gln Ser Phe Gly Met Leu Thr
 50                  55                  60

Leu Thr Asp Met Leu Asp Phe Ile Glu Phe Thr Leu Ala Thr Arg Lys
 65                  70                  75                  80

Leu Thr Gly Asn Ala Ala Ile Glu Glu Leu Thr Gly Tyr Ile Thr Asp
                 85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
            130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
            165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
            195                 200                 205

Pro Glu Gly Val Leu Ile Asp Gly Glu Leu Val Tyr His Glu Gln Val
            210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
            245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
            275                 280                 285

Glu Ile Tyr Ser Leu Pro Ala Phe Arg Leu Lys Tyr Asp Val Arg Phe
            290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
            325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
            355                 360                 365

Val Ile Asp Val Asp Leu Lys Ile Val Gly Ile Tyr Pro His Arg Lys
            370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
            405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
            435                 440                 445
```

-continued

```
Gly Arg Thr Asp Tyr Val Lys Leu Phe Leu Pro Ile Ala Ile Arg Leu
        450                 455                 460

Arg Glu Asp Lys Thr Lys Ala Asn Thr Phe Glu Asp Val Phe Gly Asp
465                 470                 475                 480

Phe His Lys Val Thr Gly Leu Gly Ser Gly Ser Ser Gly His His His
                485                 490                 495

His His His

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 35

His His His His His His
1               5
```